(12) United States Patent
Nam et al.

(10) Patent No.: US 8,793,078 B2
(45) Date of Patent: Jul. 29, 2014

(54) METHOD FOR PREDICTING ACTIVATION ENERGY USING ATOMIC FINGERPRINT DESCRIPTOR OR ATOMIC DESCRIPTOR

(75) Inventors: Ky Youb Nam, Gyeonggi-Do (KR); Kyoung Tai No, Seoul (KR); Doo Nam Kim, Seoul (KR); Won Seok Oh, Gyeonggi-Do (KR); Sung Kwang Lee, Seoul (KR); Ji Hoon Jung, Seoul (KR); Kwang Hwi Cho, Seoul (KR); Chang Joon Lee, Seoul (KR)

(73) Assignee: Bioinformatics & Molecular Design Research Center, Seoul (KR)

( * ) Notice: Subject to any disclaimer, the term of this patent is extended or adjusted under 35 U.S.C. 154(b) by 83 days.

(21) Appl. No.: 13/277,929

(22) Filed: Oct. 20, 2011

(65) Prior Publication Data

US 2012/0084012 A1    Apr. 5, 2012

Related U.S. Application Data

(63) Continuation of application No. 13/001,579, filed as application No. PCT/KR2009/006660 on Nov. 12, 2009.

(30) Foreign Application Priority Data

Nov. 12, 2008 (KR) .......................... 10-2008-0112389
Nov. 11, 2009 (KR) .......................... 10-2009-0108741

(51) Int. Cl.
*G01N 33/00* (2006.01)
*G01N 33/50* (2006.01)
*G06G 7/58* (2006.01)
*G06F 19/00* (2011.01)

(52) U.S. Cl.
CPC ............ *G06F 19/704* (2013.01); *G06F 19/709* (2013.01)
USPC ................................. 702/27; 702/19; 703/11

(58) Field of Classification Search
None
See application file for complete search history.

(56) References Cited

U.S. PATENT DOCUMENTS

2002/0040276 A1   4/2002   Ewing et al.
2008/0120041 A1   5/2008   Ridder et al.

FOREIGN PATENT DOCUMENTS

JP    2004-527835    9/2004
WO   WO02/075609   9/2002

OTHER PUBLICATIONS

D.M.F. Van Aalten et al., "PRODRG, a program for generating molecular topologies and unique molecular descriptors from coordinates of small molecules", Jrl. of Computer-Aided Molecular Design, vol. 10(3) pp. 255-262 (Jun. 1996).
Ovidiu Ivanciuc, "The neural network MolNet prediction of alkane enthalpies", Analytical Chimica Acta, vol. 384, Issue 3, pp. 271-284 (Apr. 1999).
International Search Report for PCT/KR2009/006660, mailed Jul. 15, 2010.
Office Action from Japanese Patent Application No. 2011-536243, mailed on Feb. 12, 2014.

*Primary Examiner* — Eric S Dejong
(74) *Attorney, Agent, or Firm* — Edwards Wildman Palmer LLP

(57) ABSTRACT

The present invention provides a method for constructing a database of atomic fingerprint descriptors. The invention provides a method for predicting activation energy using an atomic fingerprint descriptor and an atomic descriptor, the method comprising the steps of: (i) calculating the atomic fingerprint descriptor of a substrate; (ii) comparing the calculated atomic fingerprint descriptor with the constructed atomic fingerprint descriptor database to select an atomic position where cytochrome P450-mediated metabolism occurs; and (iii) predicting activation energy for the selected atomic position using an atomic descriptor. Also, the invention provides a method of predicting the activation energy of CYP450-mediated phase I metabolism using effective atomic descriptors. Specifically, the invention provides a method of predicting the activation energy either for cytochrome P450-mediated hydrogen abstraction or for tetrahedral intermediate formation in cytochrome P450-aromatic hydroxylation using equations including effective atomic descriptors.

23 Claims, 5 Drawing Sheets

METHOD FOR PREDICTING ACTIVATION ENERGY USING ATOMIC FINGERPRINT DESCRIPTOR OR ATOMIC DESCRIPTOR

CROSS-REFERENCES TO RELATED APPLICATIONS

This application is a continuation of Ser. No. 13/001,579, filed Jan. 6, 2011, which is the U.S. national phase application, pursuant to 35 U.S.C. §371, of PCT/KR2009/006660, filed Nov. 12, 2009, designating the United States, which claims priority to Korean Application No. 10-2008-0112389, filed Nov. 12, 2008, and Korean Application No. 10-2009-0108741, filed Nov. 11, 2009.

BACKGROUND OF THE DISCLOSURE

1. Technical Field

The present invention relates to a method for predicting the activation energy of phase I metabolism, mediated by CYP450 enzymes, using an effective atomic fingerprint descriptor or atomic descriptor.

2. Related Art

The prediction of absorption, distribution, metabolism and excretion (ADME) properties of drugs is a very important technique to shorten the drug development period and to enhance the probability of success of drug development. Among the drug's ADME properties, drug metabolism is a key determinant of metabolic stability, drug-drug interactions, and drug toxicity.

Metabolic reactions can be divided according to the reaction mechanism into two categories: aliphatic hydroxylation and aromatic hydroxylation. Also, they can be divided according to the type of reaction into the following categories: N-dealkylation, C-hydroxylation, N-oxidation, O-dealkylation and the like. In aliphatic hydroxylation, the iron (Fe) of compound I in the active site of CYP450 (cytochrome P450) is substituted with the hydrogen of the substrate, so that the substrate becomes a radical. Then, a hydroxyl group binds to the substrate to form a metabolite. In aromatic hydroxylation, the iron of compound I binds to the substrate to form a tetrahedral intermediate, and then becomes detached from the substrate while giving a hydroxyl group to the substrate, thereby forming a metabolite.

The metabolism of the compound may occur at most positions to which hydrogen is bound. The possibility of reaction at each position depends on how the compound binds well to CYP450 and how the reactivity at the bound position is high. To determine accessibility, a docking study on CYP450 can be carried out, followed by calculation of binding affinity.

Prediction of the metabolisms of external substances is important in the early stage of new drug development. Particularly, the reaction rate and regioselectivity of phase I metabolism are very important pharmacokinetic characteristics, through which the toxicity of metabolites can be predicted.

Such reaction rate and regioselectivity can be predicted from activation energy, but existing methods depend on time-consuming quantum mechanical calculations and difficult experiments. For example, K. R. Korzekwa et al. (*J. Am. Chem. Soc.* 1990, 112, 7042) reported a method of predicting the activation energy for hydrogen abstraction by quantum mechanical calculation, and T. S. Dowers et al. (*Drug Metab. Dispos.* 2004, 32, 328) reported a method of predicting the activation energy of aromatic hydroxylation by quantum mechanical calculation. However, such quantum mechanical methods perform calculations in various molecular states, and thus cannot determine accurate activation energy due to the complexity resulting from the conformational difference between these states.

Accordingly, the present inventors have developed a novel, fast and accurate model which can predict the activation energy of phase I metabolism on the basis of only the characteristics of an external substrate using an atomic fingerprint descriptor or an atomic descriptor, thereby completing the present invention.

SUMMARY OF THE DISCLOSURE

It is an object of the present invention to provide a method for constructing a database of atomic fingerprint descriptors.

Another object of the present invention is to provide a method for predicting activation energy using an atomic fingerprint descriptor and an atomic descriptor.

Still another object of the present invention is to provide a method for predicting activation energy using an atomic descriptor.

Still another object of the present invention is to provide a method of predicting i) a metabolite, ii) the relative rate of metabolism, iii) the regioselectivity of metabolism, iv) the inhibition of metabolism, v) a drug-drug interaction, and vi) the toxicity of a metabolite, through the activation energy predicted by said methods.

To achieve the above objects, the present invention provides a method for constructing a database of atomic fingerprint descriptors, the method comprising the steps of:
(i) calculating the atomic fingerprint descriptor of a substrate, which is represented by the following equation 1;
(ii) predicting activation energy for an atomic position using an atomic descriptor;
(iii) predicting cytochrome P450-mediated metabolism using the predicted activation energy; and
(iv) comparing the predicted metabolism with experimental metabolism and storing whether the metabolism occurs:

$$X_{abc} \quad \text{[Equation 1]}$$

wherein X is the chemical symbol of an atom; a is a bond indicator that indicates the number of atoms bonded; b is a ring indicator that indicates whether the atom is part of a ring; and c is an aromatic indicator that indicates whether the atom is an aromatic atom.

The metabolism in step (iii) is aliphatic hydroxylation or aromatic hydroxylation.

Also, the metabolism in step (iii) is N-dealkylation, C-hydroxylation, N-oxidation or O-dealkylation.

The present invention can be applied to all CYP 450 enzymes, and it is apparent that the present invention can be applied particularly to human CYP 450 enzymes. The cytochrome P450 enzymes according to the present invention include, but are not limited to, CYP2E1, CYP3A4, CYP2B6, CYP2C8, CYP2C9, CYP1A1, CYP1A2, CYP2C19, CYP2D6, CYP1B1, and CYP2A6.

In another aspect, the present invention provides a method for predicting activation energy using an atomic fingerprint descriptor and an atomic descriptor, the method comprising the steps of:
(i) calculating the atomic fingerprint descriptor of a substrate, which is represented by the following equation 1;
(ii) comparing the calculated atomic fingerprint descriptor with the data, constructed by said method, to select an atomic position where cytochrome P450-mediated metabolism can occur; and (iii) predicting activation energy for the selected atomic position using an atomic descriptor:

$$Xabc \quad \text{[Equation 1]}$$

wherein X is the chemical symbol of an atom; a is a bond indicator that indicates the number of atoms bonded; b is a ring indicator that indicates whether the atom is part of a ring; and c is an aromatic indicator that indicates whether the atom is an aromatic atom.

The metabolism in step (ii) is aliphatic hydroxylation or aromatic hydroxylation.

Also, the metabolism in step (ii) is N-dealkylation, C-hydroxylation, N-oxidation or O-dealkylation.

Examples of the cytochrome P450 enzyme include, but are not limited to, CYP2E1, CYP3A4, CYP2B6, CYP2C8, CYP2C9, CYP1A1, CYP1A2, CYP2C19, CYP2D6, CYP1B1, and CYP2A6.

In step (iii), the activation energy for cytochrome P450-mediated hydrogen abstraction from a substrate of the following formula 1 can be predicted using the atomic descriptors $[\delta_{het}]$, $[\max(\delta_{heavy})]$, $[\mu_{C-H}]$ and $$\left[\sum_{i}^{R.C.} \alpha_i\right]:$$

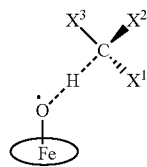

[Formula 1]

wherein the circle together with Fe—O indicates an oxyferryl intermediate; $[\delta_{het}]$ indicates the net atomic charge of a heteroatom in the alpha-position relative to the reaction center; $[\max(\delta_{heavy})]$ indicates the highest atomic charge in $X^1$, $X^2$ and $X^3$ which are neither hydrogen nor helium; $[\mu_{C-H}]$ indicates the bond dipole of the carbon-hydrogen bond; and $$\left[\sum_{i}^{R.C.} \alpha_i\right]$$

indicates the sum of the atomic polarizabilities of H, C, $X^1$, $X^2$ and $X^3$.

According to the present invention, the atomic descriptors $[\delta_{het}]$ and $[\max(\delta_{heavy})]$ can be calculated, and activation energy can be calculated according to the following equation 1-1:

$$E_a^{Habs\_(B)} = 25.94 + 1.88*[\delta_{het}] + 1.03*[\max(\delta_{heavy})]$$

wherein $E_a^{Habs\_(B)}$ indicates activation energy required for abstraction of hydrogen attached to a carbon atom having a heteroatom in the alpha-position relative to the reaction center.

Also, according to the present invention, the atomic descriptors $[\mu_{C-H}]$ and $$\left[\sum_{i}^{R.C.} \alpha_i\right]$$

can be calculated, and activation energy can be calculated according to the following equation 1-2:

$$E_a^{Habs\_(A)} = 28.50 - 2.22*[\mu_{C-H}] + 1.12*\left[\sum_{i}^{R.C.} \alpha_i\right] \quad \text{[Equation 1-2]}$$

wherein $E_a^{Habs\_(A)}$ indicates activation energy required for abstraction of hydrogen attached to a carbon atom having no heteroatom in the alpha-position relative to the reaction center.

In step (iii), the activation energy for tetrahedral intermediate formation in cytochrome P450-mediated aromatic hydroxylation for a substrate of the following formula 2 can be predicted using the atomic descriptors $[\delta_H]$ and $[\text{mean}(\alpha_{alpha})]$:

[Formula 2]

wherein the circle together with Fe—O indicates an oxyferryl intermediate; $[\delta_H]$ indicates the net atomic charge of the hydrogen of the substrate; and $[\text{mean}(\alpha_{alpha})]$ indicates the mean value of the polarizabilities of adjacent carbon atoms.

According to the present invention, the atomic descriptors $[\delta_H]$ and $[\text{mean}(\alpha_{alpha})]$ can be calculated, and activation energy can be calculated according to the following equations:

$$E_a^{aro\_o,p} = 21.34 - 0.75*[\delta_H] - 1.24*[\text{mean}(\alpha_{alpha})] \quad \text{[Equation 2-1]}$$

$$E_a^{arom} = 22.14 - 0.68*[\delta_H] - 0.83*[\text{mean}(\alpha_{alpha})] \quad \text{[Equation 2-2]}$$

$$E_a^{aro\_0,2,3} = 21.02 - 1.49*[\delta_H] - 0.92*[\text{mean}(\alpha_{alpha})] \quad \text{[Equation 2-3]}$$

wherein $E_a^{aro\_o,p}$ indicates the activation energy for tetrahedral intermediate formation in a benzene having one substituent in the ortho/para-position; $E_a^{aro\_m}$ indicates the activation energy for tetrahedral intermediate formation in a benzene having one substituent in the meta-position; and $E_a^{aro\_0,2,3}$ indicates the activation energy for tetrahedral intermediate formation in a benzene having 0, 3 or 3 substituents.

In another aspect, the present invention provides a method for predicting a metabolite using the activated energy predicted by said method. Herein, an atomic position having the lowest activation energy can be predicted as a position where metabolism occurs.

In still another aspect, the present invention provides a method of predicting a drug-drug interaction through the activation energy predicted by said method.

As used herein, the term "drug-drug interaction" refers to the effects that occur when two or more drugs are used at the same time. Such effects include changes in the kinetics of drug absorption by the intestinal tract, changes in the rate of detoxification and elimination of the drug by the liver or other organs, new or enhanced side effects and changes in the drug's activity. CYP2C9 which is a CYP isoform is one of the major enzymes that are involved in the phase I metabolism of drugs. The inhibition of this enzyme can result in an undesirable drug-drug interaction or drug toxicity [see Lin, J. H.; Lu, A. Y. H., Inhibition and induction of cytochrome P450 and the clinical implications. Clin. Pharmacokinet. 1998, 35 (5), 361-390]. Namely, if the activation energy of a substrate is relatively high, metabolism can be inhibited to result in the inhibition of CYP450 enzymes, thus causing an undesirable drug-drug interaction.

Also, metabolites, obtained by oxidation or reduction of substrates by cytochromes, can cause toxicities such as chemical carcinogenesis or mutagenesis, and for this reason, it is very important to predict metabolites, including substrate specificity for cytochromes (Vermeulen N P E, Donne-Op den Kelder G, Commandeur J N M. Molecular mechanisms of toxicology and drug design, in *Trend in Drug Research*, Proc. 7$^{th}$ Noordwijkerhout-Camerino Symp., Claassen, V., Ed., Elsevier Science Publishers, Amsterdam, 1990, 253).

The present invention provides a method of predicting a metabolite of a CYP450 enzyme by predicting binding possibility using an atomic-type fingerprint descriptor, which includes the type of atom and the surrounding bond order, and by predicting reactivity using an atomic descriptor. The method of the present invention solves a time-consuming problem in predicting accessibility using the three-dimensional structure of a CYP450 enzyme and does not require any quantum mechanical calculation or experiment.

The atomic fingerprint descriptor for predicting the possibility of binding of a cytochrome P450 enzyme to a substrate can be expressed as follows:

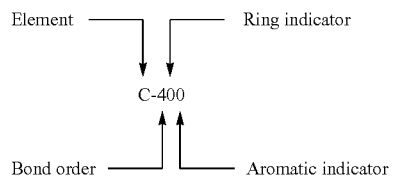

The atomic fingerprint descriptor consists of: the element symbol of an atom; a bond order indicating the number of atoms bonded; a ring indicator that indicates whether the atom is part of a ring; and an aromatic indicator that indicates whether the atom is one included in an aromatic group. This expression method intuitively and simply expresses the type of atom and the surrounding bonding environment. However, the atomic fingerprint descriptor has its own information, but does not have the surrounding bonded atoms, and for this reason, the surrounding environment is reflected by writing the surrounding bonded atomic fingerprint descriptors therewith. The larger the connectivity, the more the information of the surrounding environment is included. However, if atomic fingerprint descriptors become excessively large, over-fitting can occur. In the present invention, when the information of atoms connected directly to the atomic fingerprint descriptor was used, the most efficient calculation results were shown.

If atomic fingerprint descriptors for all the atomic positions of a substrate are the same as the atomic fingerprint descriptions of the metabolism of the substrate used in a training set, it is determined to be "on", and if not so, it is determined to be "off". Then, since the positions where metabolic reactions can occur were determined, the prediction of reactivity is performed by calculating activation energy, and the relative order of priority is determined.

Prediction of the reactivity of cytochrome P450 enzymes with the substrates was carried out using the calculation methods described in Korean Patent Application No. 10-2008-0112389 (entitled "Method for predicting activation energy using effective atomic descriptors).

Finally, the prediction of metabolic reactions of cytochrome P450 enzymes with the substrates is performed through the prediction of binding possibility and the prediction of reactivity, and the activation energies of individual positions are calculated using reactivity prediction models. The activation energies are arranged in the order of lower to higher energy, and three positions having lower activation energies are determined to be positions at which metabolic reactions can occur. The analysis of the results is carried out by determining whether the two positions selected as described include an experimentally known metabolic position.

To achieve another object, the present invention provides a method of predicting the activation energy for CYP450-mediated hydrogen abstraction according to an equation including an effective atomic descriptor. This method of the present invention is fast and accurate and does not require any quantum mechanical calculation or experiment.

Hydrogen abstraction by a cytochrome P450 enzyme may be shown in the following reaction scheme 1:

[Reaction scheme 1]

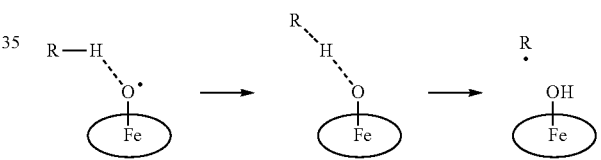

wherein the circle together with Fe—O indicates an oxyferryl intermediate.

The present invention provides a method of predicting the activation energy for cytochrome P450-mediated hydrogen abstraction from a substrate of the following formula 1 using the atomic descriptors $[\delta_{het}]$, $[\max(\delta_{heavy})]$, $[\mu_{C-H}]$ and $$\left[\sum_{i}^{R.C.} \alpha_i\right]:$$

[Formula 1]

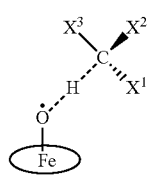

wherein the circle together with Fe—O indicates an oxyferryl intermediate; $[\delta_{het}]$ indicates the net atomic charge of a heteroatom in the alpha-position relative to the reaction center; $[\max(\delta_{heavy})]$ indicates the highest atomic charge in $X^1$, $X^2$ and $X^3$ which are neither hydrogen nor helium; $[\mu_{C-H}]$ indicates the bond dipole of the carbon-hydrogen bond; and $$\left[\sum_{i}^{R.C.} \alpha_i\right]$$

indicates the sum of the atomic polarizabilities of the atoms H, C, $X^1$, $X^2$ and $X^3$.

The present invention can be applied to all CYP 450 enzymes, and it is apparent that the present invention can be applied particularly to human CYP 450 enzymes. The cytochrome P450 enzymes according to the present invention include, but are not limited to, CYP2E1, CYP3A4, CYP2B6, CYP2C8, CYP2C9, CYP1A1, CYP1A2, CYP2C19, CYP2D6, CYP1B1, and CYP2A6.

In the method of predicting the activation energy, any C—H bond to a target molecule can be recognized as a position where metabolism can occur in the target molecule. If the C atom of the C—H bond of the target molecule is aliphatic carbon, it can be determined to be a position where hydrogen abstraction can occur.

In hydrogen abstraction by the CYP450 enzyme, the type of atom can be determined depending on whether a heteroatom is present or not in the alpha-position with respect to the reaction center (C—H where actual metabolism occurs).

If there is a heteroatom in the alpha-position relative to the reaction center, the atomic descriptors $[\delta_{het}]$ and $[\max(\delta_{heavy})]$ can be calculated, and the activation energy for hydrogen abstraction can be predicted according to the following equation 1-1:

$$E_a^{Habs\_(B)} = 25.94 + 1.88*[\delta_{het}] + 1.03*[\max(\delta_{heavy})] \quad \text{[Equation 1-1]}$$

wherein $E_a^{Habs\_(B)}$ indicates activation energy required for abstraction of hydrogen attached to a carbon atom having a heteroatom in the alpha-position relative to the reaction center.

If there is no heteroatom in the alpha-position relative to the reaction center, the atomic descriptors can be calculated, and the activation energy for hydrogen abstraction can be predicted according to the following equation [1-2]:

$$E_a^{Habs\_(A)} = 28.50 - 2.22*[\mu_{C-H}] + 1.12*\left[\sum_{i}^{R.C.} \alpha_i\right] \quad \text{[Equation 1-2]}$$

wherein $E_a^{Habs\_(A)}$ indicates activation energy required for abstraction of hydrogen attached to a carbon atom having no heteroatom in the alpha-position relative to the reaction center.

To achieve another object, the present invention provides a method of predicting the activation energy for CYP450-mediated aromatic hydroxylation according to an equation including an effective atomic descriptor. The method of the present invention is fast and accurate and does not require any quantum mechanical calculation or experiment.

The tetrahedral intermediate formation reaction in cytochrome P450-mediated aromatic hydroxylation may be shown in the following reaction scheme 2:

[Reaction scheme 2]

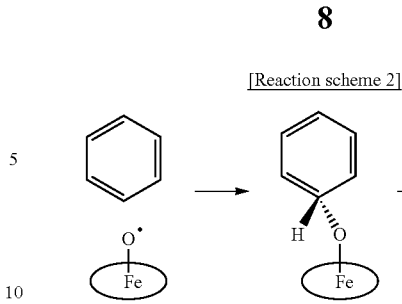

wherein the circle together with Fe—O indicates an oxyferryl intermediate.

The present invention provides a method of predicting the activation energy for tetrahedral intermediate formation in cytochrome P450-mediated aromatic hydroxylation for a substrate of the following formula 2 using the atomic descriptors $[\delta_H]$ and $[\text{mean}(\alpha_{alpha})]$:

[Formula 2]

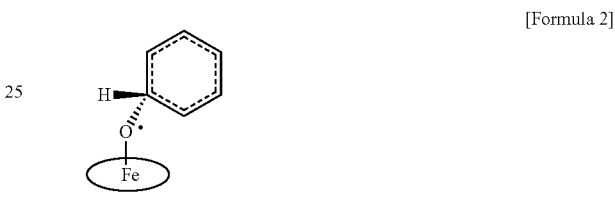

wherein the circle together with Fe—O indicates an oxyferryl intermediate; $[\delta_H]$ indicates the net atomic charge of the hydrogen; and $[\text{mean}(\alpha_{alpha})]$ indicates the mean value of the polarizabilities of adjacent carbon atoms.

The present invention may be applied to all CYP 450 enzymes, and it is apparent that the present invention can be applied particularly to human CYP 450 enzymes. The cytochrome P450 enzymes according to the present invention include, but are not limited to, CYP2E1, CYP3A4, CYP2B6, CYP2C8, CYP2C9, CYP1A1, CYP1A2, CYP2C19, CYP2D6, CYP1B1, and CYP2A6.

In the method of predicting the activation energy for tetrahedral intermediate formation, any C—H bond to a target molecule can be determined to be a position where metabolism can occur in the target molecule. Also, if the C atom of the C—H bond of the target molecule is aromatic carbon, it can be determined to be a metabolic position where aromatic hydroxylation can occur.

According to the present invention, the atomic descriptors $[(\delta_H]$ and $[\text{mean}(\alpha_{alpha})]$ can be calculated, and the activation energy can be predicted according to the following equations:

$$E_a^{aro-o,p} = 21.34 - 0.75*[\delta_H] - 1.24*[\text{mean}(\alpha_{alpha})] \quad \text{[Equation 2-1]}$$

$$E_a^{aro-m} = 22.14 - 0.68*[\delta_H] - 0.83*[\text{mean}(\alpha_{alpha})] \quad \text{[Equation 2-2]}$$

$$E_a^{aro-0,2,3} = 21.02 - 1.49*[\delta_H] - 0.92*[\text{mean}(\alpha_{alpha})] \quad \text{[Equation 2-3]}$$

wherein $E_a^{aro-o,p}$ indicates the activation energy for tetrahedral intermediate formation in a benzene having one substituent in the ortho/para-position; $E_a^{aro-m}$ indicates the activation energy for tetrahedral intermediate formation in a benzene having one substituent in the meta-position; and $E_a^{aro-m}$ indicates the activation energy for tetrahedral intermediate formation in a benzene having 0, 2 or 3 substituents.

In another aspect, the present invention provides a method of predicting the relative rate of metabolism (k) according to the following Arrhenius equation 2 using the activation energy predicted by said method:

$$k = Ae^{-E_a/RT} \quad \text{[Equation 2]}$$

wherein k is a reaction rate constant, A is a frequency factor, $E_a$ is activation energy, R is a gas constant, and T is absolute temperature.

The reason why the above equation 2 was designed is because of the atomic fraction $f=e^{-E_a/RT}$ exceeding activation energy. Namely, because only a molecule exceeding activation energy can cause a reaction, the reaction rate constant is determined by the ratio exceeding activation energy.

In another aspect, the present invention provides a method of predicting metabolic regioselectivity using the activation energy predicted by said method.

More specifically, the present invention provides a method of predicting the relative rate of metabolism according to the Arrhenius equation using the activation energy predicted by said method and predicting metabolic regioselectivity according to the following reaction scheme 3 and equation 3 using the predicted relative rate of metabolism:

[Reaction scheme 3]

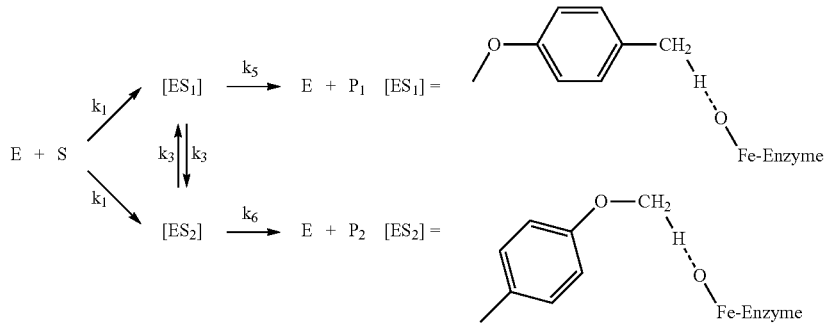

$$\frac{P_1}{P_2} = \frac{[ES_1]}{[ES_2]} \frac{k_5}{k_6} \quad \text{[Equation 3]}$$

wherein P indicates the relative probability of formation of any metabolite of all possible metabolites of a substrate, E is an enzyme, S is a substrate, ES is an enzyme-substrate complex, [ES] is the concentration of the enzyme-substrate complex, and k is a reaction rate constant.

Namely, once the reaction rate of each atom in one molecule is determined according to the Arrhenius equation, the regioselectivity in the molecule can be determined, because metabolism occurs as the reaction rate decreases. [see Higgins, L.; Korzekwa, K. R.; Rao, S.; Shou, M.; Jones, J. P., An assessment of the reaction energetics for cytochrome P450-mediated reactions. Arch. Biochem. Biophys. 2001, 385, 220-230].

In still another aspect, the present invention provides a method of predicting the inhibition of metabolism using the activation energy predicted by said method. For example, it can be predicted that, if a substrate has relatively high activation energy, the substrate will not be metabolized, and thus will remain in the active site of CYP450 enzymes.

In still another aspect, the present invention provides a method of predicting a drug-drug interaction using the activation energy predicted by said method.

As used herein, the term "atomic fingerprint descriptor" refers to a value defined to express the type of atom and the surrounding bonding environment. It consists of the element symbol of an atom, a bond order indicating the number of atoms bonded, a ring indicator that indicates whether the atom is part of a ring, and an aromatic indicator that indicates whether the atom is one included in an aromatic group.

As used herein, the term "atomic descriptor" refers to a value defined to reflect the properties of an atom itself and the bonding environment of the atom. Examples of atomic descriptors that are used in the present invention include, but are not limited to, $[\delta_{het}]$, $[\max(\delta_{heavy})]$, $[\mu_{C-H}]$, $$\left[\sum_i^{R.C.} \alpha_i\right],$$

$[\delta_H]$, $[\text{mean}(\alpha_{alpha})]$, etc.

BRIEF DESCRIPTION OF THE DRAWINGS

The above and other objects, features and advantages of the present invention will be more clearly understood from the following detailed description taken in conjunction with the accompanying drawing, in which.

DETAILED DESCRIPTION OF THE DISCLOSURE

Hereinafter, the elements and technical features of the present invention will be described in further detail with reference to examples. It is to be understood, however, that these examples are for illustrative purposes only and are not to be construed to limit the scope of the present invention. All literature cited herein is incorporated by reference.

EXAMPLES

Example 1

Construction of Database of Atomic Fingerprint Descriptors

Figure 1:
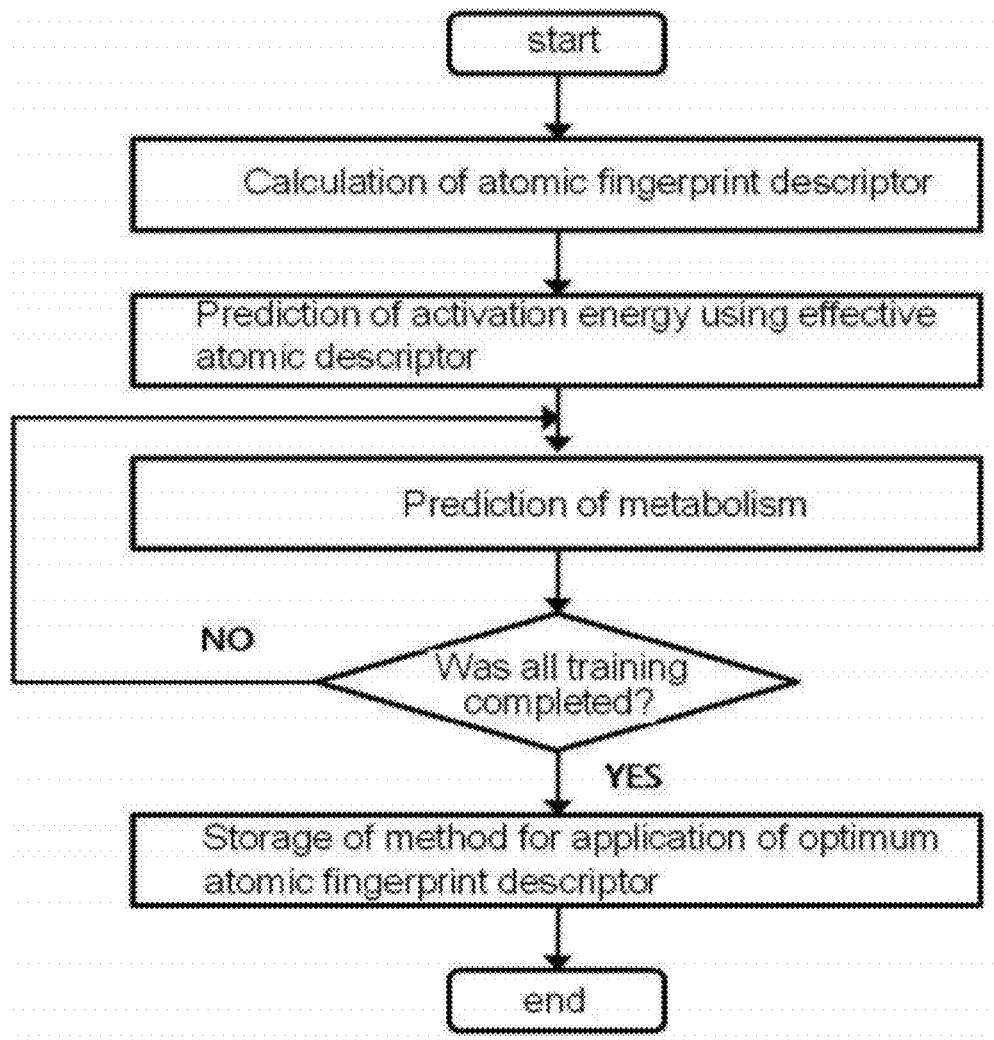
FIG. 1 is a flowchart showing a method of constructing a database of atomic fingerprint descriptors according to the present invention.

As shown in FIG. 1, the present inventors constructed a database of atomic fingerprint descriptors through a training method comprising the following steps (see FIG. 1):

(i) calculating the atomic fingerprint descriptor of a substrate, which is represented by the following equation 1;

(ii) predicting activation energy for an atomic position using an atomic descriptor;

(iii) predicting cytochrome P450-mediated metabolism using the predicted activation energy; and (iv) comparing the predicted metabolism with experimental metabolism and storing whether the predicted metabolism occurs:

$$X_{abc} \qquad \text{[Equation 1]}$$

wherein X is the chemical symbol of an atom; a is a bond order that indicates the number of atoms bonded; b is a ring indicator that indicates whether the atom is part of a ring; and c is an aromatic indicator that indicates whether the atom is an aromatic atom.

Using the above-constructed database of atomic fingerprint descriptors, the possibility of reaction of the atomic fingerprint descriptor of a given substrate with each CYP450 isoform was analyzed.

In Table 1 above, "1" indicates that, in a training set, there is a case in which a reaction occurred in a site having the relevant atomic fingerprint descriptor. "−1" indicates that, in a training set, there is no case in which a reaction occurred in a site having the relevant atomic fingerprint descriptor. "0" indicates that an atom having the relevant atomic fingerprint descriptor does not exist in a training set.

Example 2

Figure 2:
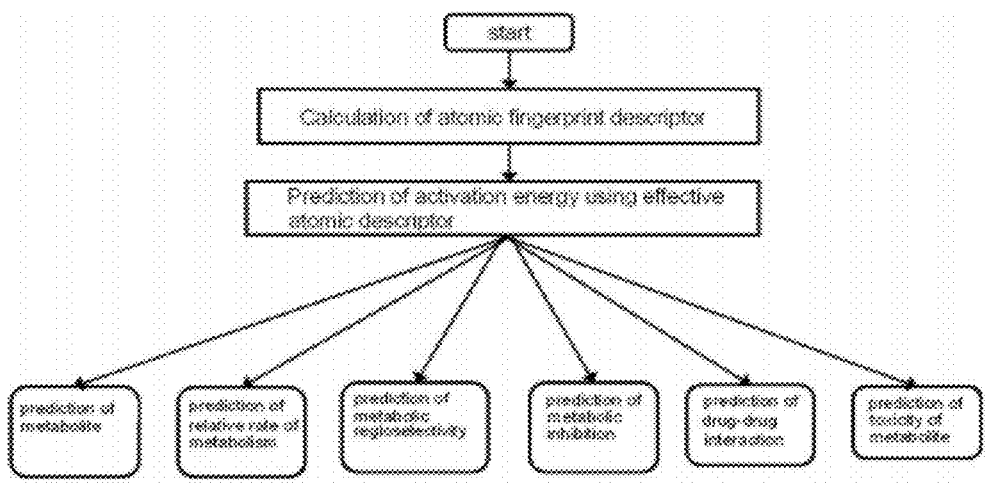
FIG. 2 is a flowchart showing a method of predicting activation energy using an atomic fingerprint descriptor and an atomic descriptor according to the present invention and predicting i) a metabolite, ii) the relative rate of metabolism, iii) the regioselectivity of metabolism, iv) the inhibition of metabolism, v) a drug-drug interaction, and vi) the toxicity of a metabolite.

Prediction of Metabolite of 2-methoxyamphetamine Using the Prediction Method of the Present Invention As shown in FIG. 2, the present inventors predicted activation energy using a method comprising the following steps (see FIG. 2):

(i) calculating the atomic fingerprint descriptor of a substrate, which is represented by the following formula 1;

(ii) comparing the calculated atomic fingerprint descriptor with the data, constructed by the method of Example 1, to select an atomic position where cytochrome P450-mediated metabolism can occur; and (iii) predicting activation energy for the selected atomic position using an atomic descriptor:

$$X_{abc} \qquad \text{[Equation 1]}$$

wherein X is the chemical symbol of an atom; a is a bond order that indicates the number of atoms bonded; b is a ring indicator that indicates whether the atom is part of a ring; and c is an aromatic indicator that indicates whether the atom is an aromatic atom.

After predicting the activation energy of 2-methoxyamphetamine using the above method, the metabolite of 2-methoxyamphetamine was predicted. 2-methoxyamphetamine has a chemical structure of the following formula 3:

TABLE 1

Results of analysis for possibility of reaction of a given substrate using constructed atomic fingerprint descriptor database

| NO. | Atomic fingerprint descriptors | CYP1A2 | CYP2C9 | CYP2D6 | CYP3A4 |
|---|---|---|---|---|---|
| 1 | C400C400H100H100H100 | 1 | 1 | −1 | 1 |
| 2 | C400C361C400H100H100 | 1 | 1 | −1 | 1 |
| 3 | C361C361C361H100 | 1 | 1 | 1 | 1 |
| 4 | C400C361H100H100H100 | 1 | 1 | 1 | 1 |
| 5 | C460C460H100H100N360 | −1 | 1 | 1 | 1 |
| 6 | C361C361H100N261 | −1 | −1 | −1 | 1 |
| 7 | C460C460C460C460H100 | −1 | −1 | −1 | −1 |
| 8 | C460C361C460C460H100 | −1 | −1 | −1 | −1 |
| 9 | C400C460H100H100H100 | −1 | −1 | −1 | −1 |
| 10 | C400C400C400H100H100 | 1 | 1 | 1 | 1 |
| 11 | C460C360C460H100H100 | 1 | 1 | 1 | 1 |
| 12 | C360C360C460H100 | 1 | 0 | −1 | 1 |
| 13 | C300C360H100O100 | 0 | 0 | 0 | 1 |
| 14 | C400C400C400H100N300 | 1 | 1 | 1 | 1 |
| 15 | C400H100H100H100O200 | 1 | 1 | 1 | 1 |
| 16 | C400C400H100H100N300 | 1 | 1 | 1 | 1 |
| 17 | C400C351C400H100H100 | −1 | 1 | −1 | −1 |
| 18 | C361C351C361H100 | 1 | −1 | 1 | 1 |
| 19 | C351C351H100N351 | −1 | −1 | −1 | −1 |
| 20 | C400H100H100H100N300 | 1 | 1 | 1 | 1 |
| 21 | C460C400C460C460H100 | 0 | −1 | −1 | −1 |
| 22 | C460C460C460H100H100 | −1 | −1 | 1 | 1 |
| 23 | C460C360C460C460H100 | 0 | −1 | 0 | −1 |

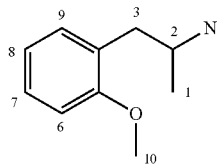

[Formula 3]

First, the positions of carbon atoms having hydrogen at positions 1, 2, 3, 6, 7, 8, 9 and 10 were examined.

Then, the atomic fingerprint descriptors of positions 1, 2, 3, 6, 7, 8, 9 and 10 were calculated and compared with the atomic fingerprint descriptor database constructed in Example 10, thereby selecting an atomic position where metabolism may occur (see Table 1).

TABLE 2

Selection of atomic positions having the possibility of metabolism through the comparison of atomic fingerprint descriptors

| Atomic position | Atomic fingerprint descriptor | Results of comparison | Possibility of metabolism |
| --- | --- | --- | --- |
| Atom 1 | C400C400H100H100H100 | −1 | Impossible |
| Atom 2 | C400C400C400H100N300 | 1 | Possible |
| Atom 3 | C400C361C400H100H100 | −1 | Impossible |
| Atom 6 | C361C361C361H100 | 1 | Possible |
| Atom 7 | C361C361C361H100 | 1 | Possible |
| Atom 8 | C361C361C361H100 | 1 | Possible |
| Atom 9 | C361C361C361H100 | 1 | Possible |
| Atom 10 | C400H100H100H100O200 | 1 | Possible |

Then, the activation energies of the atomic positions having the possibility of metabolism were calculated.

TABLE 3

Calculation of activation energies of atomic positions having the possibility of metabolism (see Example 6)

| Atomic position | Activation energy |
| --- | --- |
| Atom 2 | 22.93 |
| Atom 6 | 25.60 |
| Atom 7 | 27.42 |
| Atom 8 | 27.25 |
| Atom 9 | 27.30 |
| Atom 10 | 22.22 |

Then, atomic position 10 having the lowest activation energy was predicted as a position where a reaction occurs. Also, the following metabolite (formula 4) where O-dealkylation occurred at position 10 was predicted in the following manner.

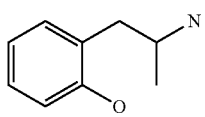

[Formula 4]

Example 3

Prediction of Metabolite Using Only Reactivity Prediction Model

A metabolite was predicted only with a reactivity prediction model without considering the binding possibility of a substrate. When analysis was carried out using a method of selecting two positions having the highest possibility, a predictability of about 62-70% was generally shown.

TABLE 4

Results of metabolite prediction carried out using only reactivity prediction model

| | $N^a$ | $Nc^b$ | Nc/N(%) |
| --- | --- | --- | --- |
| CYP1A2 | 144 | 101 | 70.1 |
| CYP2C9 | 119 | 83 | 69.7 |
| CYP2D6 | 146 | 91 | 62.3 |
| CYP3A4 | 196 | 128 | 65.3 |

[a]Number of substrates used in training;
[b]Number of substrates that accurately reproduced an experimentally known metabolism.

Example 4

Prediction of Metabolite Using Accessibility Prediction Model and Reactivity Prediction Model In order to add the possibility of binding of various CYP450 enzymes to substrates, atomic fingerprint descriptors were used. A total of 185 atomic fingerprint descriptors were used, and the possibility of metabolism by each CYP450 isoform was analyzed. Using a combination of an accessibility prediction model and a reactivity prediction model, two positions having the highest possibility and experimentally known metabolic positions were comparatively analyzed, and the results of the analysis are shown in Table 5 below.

TABLE 5

| | $N^a$ | $Nc^b$ | Nc/N(%) |
| --- | --- | --- | --- |
| CYP1A2 | 144 | 112 | 77.8 |
| CYP2C9 | 119 | 92 | 77.3 |
| CYP2D6 | 146 | 102 | 69.9 |
| CYP3A4 | 196 | 145 | 74.0 |

[a]Number of substrates used in training;
[b]Number of substrates that accurately reproduced an experimentally known metabolism.

Generally, a predictability of 70-78% was shown, and the predictability was more than 5% higher than that of Example 3 in which only the reactivity prediction model was used.

For reference, the substrates used in the metabolite prediction training according to each cytochrome P450 isoform in Tables 4 and 5 above are shown in the following Tables.

TABLE 6

Substrates used in training for prediction of metabolites with CYP1A2 (144 cases)

| | Substrate |
| --- | --- |
| 1 | 1-ethylpyrene |
| 2 | 1-methylpyrene |
| 3 | 2,3,7-trichlorooxanthrene |
| 4 | (5S)-5-(3-hydroxyphenyl)-5-phenylimidazolidine-2,4-dione |
| 5 | (5S)-5-(4-hydroxyphenyl)-5-phenylimidazolidine-2,4-dione |

TABLE 6-continued

Substrates used in training for prediction of metabolites with CYP1A2 (144 cases)

| | Substrate |
|---|---|
| 6 | 7-ethoxy-4-(trifluoromethyl)-2H-chromen-2-one |
| 7 | 7-ethoxycoumarin |
| 8 | 7-ethoxyresorufin |
| 9 | 7-methoxyresorufin |
| 10 | 1-[(2S)-4-(5-benzylthiophen-2-yl)but-3-yn-2-yl]urea |
| 11 | aflatoxin-b1 |
| 12 | all-trans-retinol |
| 13 | almotriptan |
| 14 | Ametryne |
| 15 | amitriptyline |
| 16 | amodiaquine |
| 17 | Antipyrine |
| 18 | Apigenin |
| 19 | atomoxetine |
| 20 | Atrazine |
| 21 | Azelastine |
| 22 | 7-(benzyloxy)-4-(trifluoromethyl)-2H-chromen-2-one |
| 23 | Biochainin-a |
| 24 | bropirimine |
| 25 | Bufuralol |
| 26 | Bunitrolol |
| 27 | bupivacaine |
| 28 | Capsaicin |
| 29 | carbamazepine |
| 30 | Carbaryl |
| 31 | Carbofuran |
| 32 | Carvedilol |
| 33 | 7-ethoxy-2-oxo-2H-chromene-3-carbonitrile |
| 34 | Celecoxib |
| 35 | chloroquine |
| 36 | chlorpromazine |
| 37 | chlorpropamide |
| 38 | Cilostazol |
| 39 | Cisapride |
| 40 | clomipramine |
| 41 | clozapine |
| 42 | 2-chloro-3-(pyridin-3-yl)-5,6,7,8-tetrahydroindolizine-1-carboxamide |
| 43 | curcumin |
| 44 | cyclobenzaprine |
| 45 | dacarbazine |
| 46 | dimethyl 7,7'-dimethoxy-4,4'-bi-1,3-benzodioxole-5,5'-dicarboxylate |
| 47 | deprenyl |
| 48 | dextromethorphan |
| 49 | dibenzo-a-h-anthracene |
| 50 | diclofenac |
| 51 | dihydrodiol |
| 52 | dimethoxyisoflavone |
| 53 | dimethyloxoxanthene |
| 54 | dimmamc |
| 55 | domperidone |
| 56 | doxepin |
| 57 | eletriptan |
| 58 | ellipticine |
| 59 | estradiol-methyl-ether |
| 60 | estrone |
| 61 | etoricoxib |
| 62 | fenproporex |
| 63 | fluoxetine |
| 64 | flurbiprofen |
| 65 | formononetin |
| 66 | N-[2-(5-methoxy-1H-indol-3-yl)ethyl]-N-(propan-2-yl)propan-2-amine |
| 67 | galangin |
| 68 | genistein |
| 69 | 2-[(R)-{[5-(cyclopropylmethoxy)pyridin-3-yl]methyl}sulfinyl]-5-fluoro-1H-benzimidazole |
| 70 | harmaline |
| 71 | harmine |
| 72 | hesperetin |
| 73 | imipramine |
| 74 | kaempferide |
| 75 | kaempferol |
| 76 | N-carbamimidoyl-4-cyano-1-benzothiophene-2-carboxamide |
| 77 | levobupivacaine |
| 78 | lidocaine |
| 79 | loratadine |
| 80 | 4-(aminomethyl)-7-methoxy-2H-chromen-2-one |
| 81 | maprotiline |
| 82 | (2R)-1-(1,3-benzodioxol-5-yl)-N-ethylpropan-2-amine |
| 83 | (2R)-1-(1,3-benzodioxol-5-yl)-N-methylpropan-2-amine |
| 84 | 3,8-dimethyl-3H-imidazo[4,5-f]quinoxalin-2-amine |
| 85 | melatonin |
| 86 | mephenytoin |
| 87 | methoxychlor |
| 88 | methoxychlor-mono-oh |
| 89 | methyleugenol |
| 90 | metoclopramide |
| 91 | mexiletine |
| 92 | mianserin |
| 93 | mirtazapine |
| 94 | (2S)-1-(4-methylphenyl)-2-(pyrrolidin-1-yl)propan-1-one |
| 95 | 1-methyl-4-phenyl-1,2,3,6-tetrahydropyridine |
| 96 | n-nitrosodiamylamine |
| 97 | naproxen |
| 98 | naringenin |
| 99 | nefiracetam |
| 100 | nn-dimethyl-m-toluamide |
| 101 | 4-[methyl(nitroso)amino]-1-(pyridin-3-yl)butan-1-one |
| 102 | nordiazepam |
| 103 | nortriptyline |
| 104 | ochratoxin-a |
| 105 | olanzapine |
| 106 | olopatadine |
| 107 | (3S)-3-[3-(methylsulfonyl)phenyl]-1-propylpiperidine |
| 108 | oxycodone |
| 109 | perazine |
| 110 | perphenazine |
| 111 | phenytoin |
| 112 | 1-methyl-6-phenyl-1H-imidazo[4,5-b]pyridin-2-amine |
| 113 | pimobendan |
| 114 | progesterone |
| 115 | propafenone |
| 116 | propanolol |
| 117 | prunetin |
| 118 | pyrazoloacridine |
| 119 | quinacrine |
| 120 | ropinirole |
| 121 | ropivacaine |
| 122 | rosiglitazone |
| 123 | safrole |
| 124 | sertraline |
| 125 | sildenafil |
| 126 | stilbene |
| 127 | (3Z)-3-[(3,5-dimethyl-1H-pyrrol-2-yl)methylidene]-1,3-dihydro-2H-indol-2-one |
| 128 | tacrine |
| 129 | tamarixetin |
| 130 | tangeretin |
| 131 | tauromustine |
| 132 | terbinafine |
| 133 | terbuthylazine |
| 134 | testosterone |
| 135 | theobromine |
| 136 | theophylline |
| 137 | tolperisone |
| 138 | N-(2,6-dichlorobenzoyl)-4-(2,6-dimethoxy-phenyl)-L-phenylalanine |
| 139 | trans-retinoic-acid |
| 140 | warfarin |
| 141 | zileuton |
| 142 | zolmitriptan |
| 143 | zolpidem |
| 144 | zotepine |

TABLE 7

Substrates used in training for prediction of metabolites with CYP2C9 (119 cases)

| | Substrate |
|---|---|
| 1 | 2n-propylquinoline |
| 2 | (5S)-5-(3-hydroxyphenyl)-5-phenylimidazolidine-2,4-dione |
| 3 | (5S)-5-(4-hydroxyphenyl)-5-phenylimidazolidine-2,4-dione |
| 4 | 5-hydroxytryptamine |
| 5 | 2-(trans-4-tert-butylcyclohexyl)-3-hydroxynaphthalene-1,4-dione |
| 6 | 7-ethoxy-4-(trifluoromethyl)-2H-chromen-2-one |
| 7 | 7-ethoxycoumarin |
| 8 | 7-ethoxyresorufin |
| 9 | 9-cis-retinoic-acid |
| 10 | 1-[(2S)-4-(5-benzylthiophen-2-yl)but-3-yn-2-yl]urea |
| 11 | aceclofenac |
| 12 | Ametryne |
| 13 | amitriptyline |
| 14 | Antipyrine |
| 15 | atomoxetine |
| 16 | 7-(benzyloxy)-4-(trifluoromethyl)-2H-chromen-2-one |
| 17 | Biochainin-a |
| 18 | Bufuralol |
| 19 | Capsaicin |
| 20 | carbamazepine |
| 21 | Carvedilol |
| 22 | 7-ethoxy-2-oxo-2H-chromene-3-carbonitrile |
| 23 | Celecoxib |
| 24 | chlorpropamide |
| 25 | Cisapride |
| 26 | clomipramine |
| 27 | Clozapine |
| 28 | 2-chloro-3-(pyridin-3-yl)-5,6,7,8-tetrahydroindolizine-1-carboxamide |
| 29 | N,4-dimethyl-N-(1-phenyl-1H-pyrazol-5-yl)benzenesulfonamide |
| 30 | 2-[(3S,4R)-3-benzyl-4-hydroxy-3,4-dihydro-2H-chromen-7-yl]-4-(trifluoromethyl)benzoic acid |
| 31 | cyclophosphamide |
| 32 | dimethyl 7,7'-dimethoxy-4,4'-bi-1,3-benzodioxole-5,5'-dicarboxylate |
| 33 | Deprenyl |
| 34 | dexloxiglumide |
| 35 | dextromethorphan |
| 36 | Diazepam |
| 37 | dibenzo-a-h-anthracene |
| 38 | Diclofenac |
| 39 | Diltiazem |
| 40 | disopyramide |
| 41 | doxepin |
| 42 | eletriptan |
| 43 | ellipticine |
| 44 | estradiol |
| 45 | estradiol-methyl-ether |
| 46 | estrone |
| 47 | etodolac |
| 48 | etoperidone |
| 49 | Fluoxetine |
| 50 | flurbiprofen |
| 51 | fluvastatin |
| 52 | N-[2-(5-methoxy-1H-indol-3-yl)ethyl]-N-(propan-2-yl)propan-2-amine |
| 53 | galangin |
| 54 | 2-[(R)-{[5-(cyclopropylmethoxy)pyridin-3-yl]methyl}sulfinyl]-5-fluoro-1H-benzimidazole |
| 55 | harmaline |
| 56 | harmine |
| 57 | hydromorphone |
| 58 | ibuprofen |
| 59 | ifosfamide |
| 60 | imipramine |
| 61 | indomethacin |
| 62 | kaempferide |
| 63 | ketamine |
| 64 | (1S,4S)-(6-dimethylamino-4,4-diphenyl-heptan-3-yl)acetate |
| 65 | lansoprazole |
| 66 | lidocaine |
| 67 | loratadine |
| 68 | lornoxicam |
| 69 | losartan |
| 70 | luciferin |
| 71 | [(4E)-7-chloro-4-[(sulfooxy)imino]-3,4-dihydroquinolin-1(2H)-yl](2-methylphenyl)methanone |
| 72 | mefenamic-acid |
| 73 | melatonin |
| 74 | meloxicam |
| 75 | mephenytoin |
| 76 | methadone |
| 77 | methoxychlor-mono-oh |
| 78 | methyleugenol |
| 79 | mianserin |
| 80 | midazolam |
| 81 | mirtazapine |
| 82 | 4-{[(5S)-2,4-dioxo-1,3-thiazolidin-5-yl]methyl}-2-methox-N-[4-(trifluoromethyl)benzyl]benzamide |
| 83 | (2S)-1-(4-methylphenyl)-2-(pyrrolidin-1-yl)propan-1-one |
| 84 | n-nitrosodiamylamine |
| 85 | naproxen |
| 86 | nevirapine |
| 87 | ochratoxin-a |
| 88 | omeprazole |
| 89 | oxybutynin |
| 90 | oxycodone |
| 91 | perazine |
| 92 | perphenazine |
| 93 | phenacetin |
| 94 | phencyclidine |
| 95 | phenprocoumon |
| 96 | phenytoin |
| 97 | piroxicam |
| 98 | progesterone |
| 99 | rosiglitazone |
| 100 | (5Z)-7-[(1S,2R,3R,4R)-3-benzenesulfonamidobicyclo[2.2.1]heptan-2-yl]hept-5-enoic acid |
| 101 | sertraline |
| 102 | sildenafil |
| 103 | 7-chloro-N-({5-[(dimethylamino)methyl]cyclopenta-1,4-dien-1-yl}methyl)quinolin-4-amine |
| 104 | tamarixetin |
| 105 | tauromustine |
| 106 | temazepam |

TABLE 7-continued

Substrates used in training for prediction of metabolites with CYP2C9 (119 cases)

| | Substrate |
|---|---|
| 107 | terbinafine |
| 108 | testosterone |
| 109 | theophylline |
| 110 | tolbutamide |
| 111 | torasemide |
| 112 | N-(2,6-dichlorobenzoyl)-4-(2,6-dimethoxy-phenyl)-L-phenylalanine |
| 113 | trans-retinoic-acid |
| 114 | valdecoxib |
| 115 | valsartan |
| 116 | venlafaxine |
| 117 | vivid-red |
| 118 | warfarin |
| 119 | zolpidem |

TABLE 8

Substrates used in training for prediction of metabolites with CYP2D6 (146 cases)

| | Substrate |
|---|---|
| 1 | 2-(piperazin-1-yl)pyrimidine |
| 2 | 2-methoxyamphetamine |
| 3 | 4-methoxyamphetamine |
| 4 | 2-(5-methoxy-1H-indol-3-yl)-N,N-dimethylethanamine |
| 5 | 5-methoxytryptamine |
| 6 | 5-methoxytryptamine |
| 7 | 7-ethoxycoumarin |
| 8 | all-trans-retinol |
| 9 | all-trans-retinol |
| 10 | amitriptyline |
| 11 | amodiaquine |
| 12 | aripiprazole |
| 13 | atomoxetine |
| 14 | atrazine |
| 15 | azelastine |
| 16 | biochainin-a |
| 17 | bisoprolol |
| 18 | N-({4-[(5-bromopyrimidin-2-yl)oxy]-3-methylphenyl}carbamoyl)-2-(dimethylamino)benzamide |
| 19 | brofaromine |
| 20 | bunitrolol |
| 21 | bupivacaine |
| 22 | capsaicin |
| 23 | carbamazepcapsaicinine |
| 24 | carbamazepcapsaicinine |
| 25 | carbofuran |
| 26 | Carvedilol |
| 27 | 7-ethoxy-2-oxo-2H-chromene-3-carbonitrile |
| 28 | celecoxib |
| 29 | celecoxib |
| 30 | chlorpromazine |
| 31 | chlorpropamide |
| 32 | cibenzoline |
| 33 | cilostazol |
| 34 | cisapride |
| 35 | citalopram |
| 36 | clomipramine |
| 37 | clozapine |
| 38 | codeine |
| 39 | curcumin |
| 40 | cyclophosphamide |
| 41 | delavirdine |
| 42 | deprenyl |
| 43 | dextromethorphan |
| 44 | diclofenac |
| 45 | dihydrocodeine |
| 46 | diltiazem |
| 47 | dimmamc |
| 48 | domperidone |

TABLE 8-continued

Substrates used in training for prediction of metabolites with CYP2D6 (146 cases)

| | Substrate |
|---|---|
| 49 | doxepin |
| 50 | 2-(hydroxymethyl)-4-[5-(4-methoxyphenyl)-3-(trifluoromethyl)-1H-pyrazol-1-yl]benzenesulfonamide |
| 51 | eletriptan |
| 52 | ellipticine |
| 53 | estradiol |
| 54 | estrone |
| 55 | etoperidone |
| 56 | etoricoxib |
| 57 | eugenol |
| 58 | fenproporex |
| 59 | fluoxetine |
| 60 | fluvastatin |
| 61 | N-[2-(5-methoxy-1H-indol-3-yl)ethyl]-N-(propan-2-yl)propan-2-amine |
| 62 | galantamine |
| 63 | gefitinib |
| 64 | genistein |
| 65 | granisetron |
| 66 | harmaline |
| 67 | harmine |
| 68 | hydrocodone |
| 69 | hydromorphone |
| 70 | ibogaine |
| 71 | iloperidone |
| 72 | imipramine |
| 73 | cilostazol |
| 74 | (1S,4S)-(6-dimethylamino-4,4-diphenyl-heptan-3-yl)acetate |
| 75 | lidocaine |
| 76 | loratadine |
| 77 | 4-(aminomethyl)-7-methoxy-2H-chromen-2-one |
| 78 | maprotiline |
| 79 | (2R)-1-(1,3-benzodioxol-5-yl)-N-ethylpropan-2-amine |
| 80 | (2R)-1-(1,3-benzodioxol-5-yl)-N-methylpropan-2-amine |
| 81 | melatonin |
| 82 | mequitazine |
| 83 | meta-chlorophenylpiperazine |
| 84 | methadone |
| 85 | methadone |
| 86 | methoxychlor-mono-oh |
| 87 | methoxyphenamine |
| 88 | methyleugenol |
| 89 | metoclopramide |
| 90 | metoprolol |
| 91 | mexiletine |
| 92 | mianserin |
| 93 | minaprine |
| 94 | mirtazapine |
| 95 | (2S)-1-(4-methoxyphenyl)-2-(pyrrolidin-1-yl)propan-1-one |
| 96 | (2S)-1-(4-methylphenyl)-2-(pyrrolidin-1-yl)propan-1-one |
| 97 | 1-methyl-4-phenyl-1,2,3,6-tetrahydropyridine |
| 98 | n-nitrosodiamylamine |
| 99 | nevirapine |
| 100 | 4-[methyl(nitroso)amino]-1-(pyridin-3-yl)butan-1-one |
| 101 | nortriptyline |
| 102 | 5-(diethylamino)-2-methylpent-3-yn-2-yl(2S)-2-cyclohexyl-2-hydroxy-2-phenylacetate |
| 103 | olanzapine |
| 104 | omeprazole |
| 105 | ondansetron |
| 106 | (3S)-3-[3-(methylsulfonyl)phenyl]-1-propylpiperidine |
| 107 | oxybutynin |
| 108 | oxycodone |
| 109 | perazine |
| 110 | perphenazine |
| 111 | phenacetin |
| 112 | phencyclidine |
| 113 | phenformin |
| 114 | phenytoin |
| 115 | pinoline |
| 116 | (2R)-1-(4-methoxyphenyl)-N-methylpropan-2-amine |
| 117 | procainamide |
| 118 | progesterone |
| 119 | promethazine |
| 120 | propafenone |

TABLE 8-continued

Substrates used in training for prediction of metabolites with CYP2D6 (146 cases)

| | Substrate |
|---|---|
| 121 | propanolol |
| 122 | 3-(2-chlorophenyl)-N-[(1S)-1-(3-methoxyphenyl)ethyl]propan-1-amine |
| 123 | reduced-dolasetron |
| 124 | ropivacaine |
| 125 | sertraline |
| 126 | sildenafil |
| 127 | sparteine |
| 128 | spirosulfonamide |
| 129 | 7-chloro-N-({5-[(dimethylamino)methyl]cyclopenta-1,4-dien-1-yl}methyl)quinolin-4-amine |
| 130 | stilbene |
| 131 | stilbene |
| 132 | tangeretin |
| 133 | tauromustine |
| 134 | tegaserod |
| 135 | testosterone |
| 136 | theophylline |
| 137 | tolperisone |
| 138 | tramadol |
| 139 | traxoprodil |
| 140 | tropisetron |
| 141 | valdecoxib |
| 142 | venlafaxine |
| 143 | warfarin |
| 144 | yohimbine |
| 145 | zolpidem |
| 146 | zotepine |

TABLE 9

Substrates used in training for prediction of metabolites with CYP3A4 (196 cases)

| | Substrate |
|---|---|
| 1 | 1-ethylpyrene |
| 2 | 1-methylpyrene |
| 3 | 2n-propylquinoline |
| 4 | (5S)-5-(3-hydroxyphenyl)-5-phenylimidazolidine-2,4-dione |
| 5 | (5S)-5-(4-hydroxyphenyl)-5-phenylimidazolidine-2,4-dione |
| 6 | 5-methylchrysene |
| 7 | 1-ethoxycoumarin |
| 8 | 7-methoxyresorufin |
| 9 | 1-[(2S)-4-(5-benzylthiophen-2-yl)but-3-yn-2-yl]urea |
| 10 | 1-[(2S)-4-(5-benzylthiophen-2-yl)but-3-yn-2-yl]urea |
| 11 | acetochlor |
| 12 | adinazolam |
| 13 | aflatoxin-b1 |
| 14 | alachlor |
| 15 | alfentanil |
| 16 | all-trans-retinol |
| 17 | almotriptan |
| 18 | dextromethorphan |
| 19 | ambroxol |
| 20 | ametryne |
| 21 | amitriptyline |
| 22 | amodiaquine |
| 23 | androstenedione |
| 24 | apigenin |
| 25 | aripiprazole |
| 26 | atomoxetine |
| 27 | atrazine |
| 28 | azelastine |
| 29 | 7-(benzyloxy)-4-(trifluoromethyl)-2H-chromen-2-one |
| 30 | bisoprolol |
| 31 | N-({4-[(5-bromopyrimidin-2-yl)oxy]-3-methylphenyl}carbamoyl)-2-(dimethylamino)benzamide |
| 32 | brotizolam |
| 33 | budesonide |
| 34 | bufuralol |
| 35 | bupivacaine |

TABLE 9-continued

Substrates used in training for prediction of metabolites with CYP3A4 (196 cases)

| | Substrate |
|---|---|
| 36 | bupropion |
| 37 | capsaicin |
| 38 | carbamazepine |
| 39 | carbaryl |
| 40 | carbofuran |
| 41 | carvedilol |
| 42 | celecoxib |
| 43 | cerivastatin |
| 44 | chloroquine |
| 45 | chlorpropamide |
| 46 | cibenzoline |
| 47 | cisapride |
| 48 | citalopram |
| 49 | clobazam |
| 50 | clomipramine |
| 51 | clozapine |
| 52 | 2-chloro-3-(pyridin-3-yl)-5,6,7,8-tetrahydroindolizine-1-carboxamide |
| 53 | cocaine |
| 54 | codeine |
| 55 | colchicine |
| 56 | (3S)-3-(6-methoxypyridin-3-yl)-3-{2-oxo-3-[3-(5,6,7,8-tetrahydro-1,8-naphthyridin-2-yl)propyl]imidazolidin-1-yl}propanoic acid |
| 57 | 2-[(3S,4R)-3-benzyl-4-hydroxy-3,4-dihydro-2H-chromen-7-yl]-4-(trifluoromethyl)benzoic acid |
| 58 | diethyl({[(2R,4S,7S)-1]-ethyl-6-methyl-6,11-diazatetracyclo[7.6.1.0$^{2,7}$.0$^{12,16}$]hexadeca-1(15),9,12(16),13-tetraen-4-yl]sulfamoyl})amine |
| 59 | cyclobenzaprine |
| 60 | cyclophosphamide |
| 61 | dimethyl 7,7'-dimethoxy-4,4'-bi-1,3-benzodioxole-5,5'-dicarboxylate |
| 62 | delavirdine |
| 63 | deoxycholic-acid |
| 64 | deprenyl |
| 65 | deramciclane |
| 66 | dexamethasone |
| 67 | dexloxiglumide |
| 68 | dextromethorphan |
| 69 | dextropropoxyphene |
| 70 | (3S,8R,9S,10R,13S,14S)-3-hydroxy-10,13-dimethyl-1,2,3,4,7,8,9,11,12,14,15,16-dodecahydrocyclopenta[a]phenanthren-17-one |
| 71 | diazepam |
| 72 | dibenzo-a-h-anthracene |
| 73 | diclofenac |
| 74 | dihydrocodeine |
| 75 | dihydrodiol |
| 76 | diltiazem |
| 77 | disopyramide |
| 78 | domperidone |
| 79 | doxepin |
| 80 | ecabapide |
| 81 | eletriptan |
| 82 | ellipticine |
| 83 | eplerenone |
| 84 | estazolam |
| 85 | estradiol |
| 86 | estrone |
| 87 | etoperidone |
| 88 | etoricoxib |
| 89 | felodipine |
| 90 | fenproporex |
| 91 | fentanyl |
| 92 | finasteride |
| 93 | flucloxacillin |
| 94 | fluoxetine |
| 95 | fluvastatin |
| 96 | N-[2-(5-methoxy-1H-indol-3-yl)ethyl]-N-(propan-2-yl)propan-2-amine |
| 97 | gepirone |
| 98 | granisetron |
| 99 | 2-[(R)-{[5-(cyclopropylmethoxy)pyridin-3-yl]methyl}sulfinyl]-5-fluoro-1H-benzimidazole |

TABLE 9-continued

Substrates used in training for prediction of metabolites with CYP3A4 (196 cases)

| | Substrate |
|---|---|
| 100 | hydrocodone |
| 101 | hydromorphone |
| 102 | ibogaine |
| 103 | ifosfamide |
| 104 | iloperidone |
| 105 | imipramine |
| 106 | ketamine |
| 107 | ketobemidone |
| 108 | N-carbamimidoyl-4-cyano-1-benzothiophene-2-carboxamide |
| 109 | (1S,4S)-(6-dimethylamino-4,4-diphenyl-heptan-3-yl)acetate |
| 110 | laquinimod |
| 111 | levobupivacaine |
| 112 | lidocaine |
| 113 | lisofylline |
| 114 | ropinirole |
| 115 | loratadine |
| 116 | losartan |
| 117 | lovastatin |
| 118 | [(4E)-7-chloro-4-[(sulfooxy)imino]-3,4-dihydroquinolin-1(2H)-yl](2-methylphenyl)methanone |
| 119 | (2R)-1-(1,3-benzodioxol-5-yl)-N-ethylpropan-2-amine |
| 120 | (2R)-1-(1,3-benzodioxol-5-yl)-N-methylpropan-2-amine |
| 121 | melatonin |
| 122 | meloxicam |
| 123 | 1-(4-methoxyphenyl)piperazine |
| 124 | methadone |
| 125 | methoxychlor |
| 126 | methoxychlor-mono-oh |
| 127 | metoclopramide |
| 128 | mianserin |
| 129 | midazolam |
| 130 | mirtazapine |
| 131 | 4-{[(5S)-2,4-dioxo-1,3-thiazolidin-5-yl]methyl}-2-methoxy-N-[4-(trifluoromethyl)benzyl]benzamide |
| 132 | (2S)-1-(4-methylphenyl)-2-(pyrrolidin-1-yl)propan-1-one |
| 133 | 1-methyl-4-phenyl-1,2,3,6-tetrahydropyridine |
| 134 | mycophenolic-acid |
| 135 | n-nitrosodiamylamine |
| 136 | naringenin |
| 137 | nefiracetam |
| 138 | nn-dimethyl-m-toluamide |
| 139 | 4-[methyl(nitroso)amino]-1-(pyridin-3-yl)butan-1-one |
| 140 | diethyl{4-[(4-bromo-2-cyanophenyl)carbamoyl]benzyl}phosphonate |
| 141 | nordiazepam |
| 142 | nortriptyline |
| 143 | 5-(diethylamino)-2-methylpent-3-yn-2-yl(2S)-2-cyclohexyl-2-hydroxy-2-phenylacetate |
| 144 | ochratoxin-a |
| 145 | olanzapine |
| 146 | olopatadine |
| 147 | (1R,2R,10R,11S,14R,15R)-14-ethynyl-14-hydroxy-15-methyl-17-methylidenetetracyclo[8.7.0.0^{2,7}.0^{11,15}]heptadeca-6,12-dien-5-one |
| 148 | (3S)-3-[3-(methylsulfonyl)phenyl]-1-propylpiperidine |
| 149 | oxybutynin |
| 150 | oxycodone |
| 151 | perazine |
| 152 | perphenazine |
| 153 | phenacetin |
| 154 | phencyclidine |
| 155 | phenprocoumon |
| 156 | pimobendan |
| 157 | pradefovir |
| 158 | progesterone |
| 159 | propafenone |
| 160 | pyrazoloacridine |
| 161 | quinacrine |
| 162 | rebamipide |
| 163 | reboxetine |
| 164 | ropinirole |
| 165 | ropivacaine |
| 166 | roquinimex |
| 167 | safrole |
| 168 | safrole |

TABLE 9-continued

Substrates used in training for prediction of metabolites with CYP3A4 (196 cases)

| | Substrate |
|---|---|
| 169 | salmeterol |
| 170 | senecionine |
| 171 | seratrodast |
| 172 | seratrodast |
| 173 | seratrodast |
| 174 | 7-chloro-N-({5-[(dimethylamino)methyl]cyclopenta-1,4-dien-1-yl}methyl)quinolin-4-amine |
| 175 | tamarixetin |
| 176 | tamsulosin |
| 177 | tangeretin |
| 178 | tauromustine |
| 179 | temazepam |
| 180 | terbinafine |
| 181 | terbuthylazine |
| 182 | testosterone |
| 183 | theophylline |
| 184 | tramadol |
| 185 | trans-retinoic-acid |
| 186 | trazodone |
| 187 | triazolam |
| 188 | trofosfamide |
| 189 | tropisetron |
| 190 | valdecoxib |
| 191 | |
| 192 | |
| 193 | yohimbine |
| 194 | zaleplon |
| 195 | zolpidem |
| 196 | zotepine |

Example 5

Comparison of Existing Metabolic Prediction Model with Prediction Model of the Present Invention The present invention is an improved model compared to an existing metabolic prediction model.

The existing QSAR model (Sheridan R P, Korzekwa K R, Torres R A, Walker M J. J. Med. Chem. (2007) 50; 3173) and the present invention select two highly possible positions, and the MetaSite program (Cruciani G, Carosati E, Boeck B D, Ethirajulu K, Mackie C, Howe T, Vianello R. J. Med. Chem. (2005)48; 6970) selects three highly possible positions. Thus, these cannot be directly compared with each other, but as can be seen in Table 3 below, the present invention shows improved predictability.

TABLE 10

Comparison of existing metabolic prediction model and inventive prediction model

| | 3A4 | 2D6 | 2C9 | 1A2 |
|---|---|---|---|---|
| QSAR model[a] | 84% | 70% | 67% | — |
| MetaSite[b] | 72% | 86% | 86% | 75% |
| Invention[a] | 74% | 70% | 77% | 78% |

[a]selection of two highly possible positions
[b]selection of three highly possible positions

Example 6

Prediction of Activation Energy Using Atomic Descriptors

6-1. Prediction of Activation Energy for Hydrogen Abstraction Using Atomic Descriptors Hydrogen abstraction by a cytochrome P450 enzyme may be shown in the following reaction scheme 1:

[Reaction scheme 1]

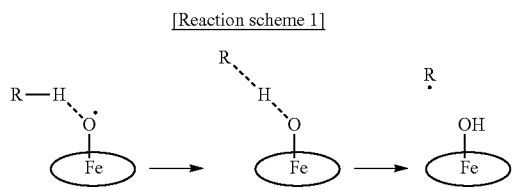

wherein the cycle together with Fe—O indicates an oxyferryl intermediate.

In the present invention, the activation energy for cytochrome P450-mediated hydrogen abstraction from a substrate of the following formula 1 was predicted using the atomic descriptors $[\delta_{het}]$, $[\max(\delta_{heavy})]$, $[\mu_{C-H}]$ and $$\left[\sum_{i}^{R.C.} \alpha_i\right]:$$

[Formula 1]

wherein the circle together with Fe—O indicates an oxyferryl intermediate;

$$E_a^{Habs\_(B)} = 25.94 + 1.88 * [\delta_{het}] + 1.03 * [\max(\delta_{heavy})]; \quad \text{[Equation 1-1]}$$

$$E_a^{Habs\_(A)} = 28.50 - 2.22 * [\mu_{C-H}] + 1.12 * \left[\sum_{i}^{R.C.} \alpha_i\right] \quad \text{[Equation 1-2]}$$

wherein $E_a^{Habs\_(B)}$ indicates activation energy required for hydrogen attached to a carbon atom having a heteroatom (an atom other than carbon) in the alpha-position relative to the reaction center; $E_a^{Habs\_(A)}$ indicates activation energy required for hydrogen attached to a carbon atom having no heteroatom (an atom other than carbon) in the alpha-position relative to the reaction center; and $[\delta_{het}]$ indicates the net atomic charge of a heteroatom (an atom other than carbon) in the alpha-position relative to the reaction center; $[\max(\delta_{heavy})]$ indicates the highest atomic charge in $X^1$, $X^2$ and $X^3$ which are neither hydrogen nor helium; $[\mu_{C-H}]$ indicates the bond dipole of the carbon-hydrogen bond; and $$\left[\sum_{i}^{R.C.} \alpha_i\right]$$

indicates the sum of the atomic polarizabilities of the atoms H, C, $X^1$, $X^2$ and $X^3$.

6-2. Prediction of Activation Energy for Tetrahedral Intermediate Formation in Aromatic Hydroxylation Using Atomic Descriptors Tetrahedral intermediate formation reaction in cytochrome P450-mediated aromatic hydroxylation may be shown in the following reaction scheme 2:

[Reaction scheme 2]
Tetrahedral intermediate formation in cytochrome-P450-mediated aromatic hydroxylation

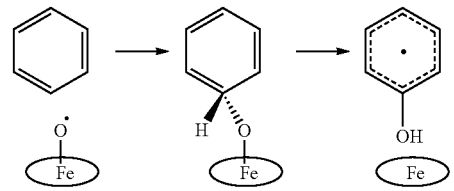

wherein the circle together with O—Fe indicates an oxyferryl intermediate.

In the present invention, the activation energy for tetrahedral intermediate formation in cytochrome P450-mediated aromatic hydroxylation of a substrate of the following formula 2 was predicted using the atomic descriptors $[\delta_H]$ and $[\text{mean}(\alpha_{alpha})]$:

[Formula 2]

wherein the circle together with Fe—O indicates an oxyferryl intermediate;

$$E_a^{aro-o,p} = 21.34 - 0.75 * [\delta_H] - 1.24 * [\text{mean}(\alpha_{alpha})] \quad \text{[Equation 2-1]}$$

$$E_a^{aro-m} = 22.14 - 0.68 * [\delta_H] - 0.83 * [\text{mean}(\alpha_{alpha})] \quad \text{[Equation 2-2]}$$

$$E_a^{aro-0,2,3} = 21.02 - 1.49 * [\delta_H] - 0.92 * [\text{mean}(\alpha_{alpha})] \quad \text{[Equation 2-3]}$$

wherein $E_a^{aro-o,p}$ indicates the activation energy for tetrahedral intermediate formation in a benzene having one substituent in the ortho/para-position; $E_a^{aro-m}$ indicates the activation energy for tetrahedral intermediate formation in a benzene having one substituent in the meta-position; $E_a^{aro-0,2,3}$ indicates the activation energy for tetrahedral intermediate formation in a benzene having 0, 2 or 3 substituents; $[\delta_H]$ indicates the net atomic charge of the hydrogen; and $[\text{mean}(\alpha_{alpha})]$ indicates the mean value of the polarizabilities of adjacent carbon atoms.

Example 7

Development of Model for Predicting Activation Energy for Hydrogen Abstraction

The activation energy for hydrogen abstraction is a good measure for predicting the regioselectivity of aliphatic hydroxylation and dehydroxylation in phase I metabolism.

[Reaction scheme 1]
Hydrogen abstraction by cytochrome P450

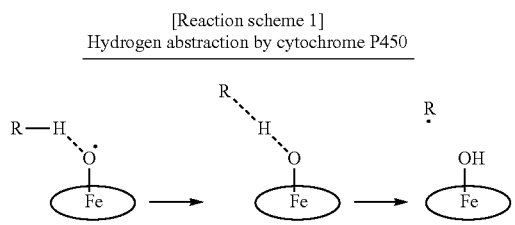

wherein the circle together with Fe—O indicates an oxyferryl intermediate.

In order to model the above reaction, the activation energies of 431 cases of 119 molecules were calculated using the AM1 (Austin Model 1) molecular orbital method.

Herein, the term "cases" refers to the number of atoms. For example, if there are 3 molecules having 3, 4 and 7 atoms, respectively, there will be 14 cases of 3 molecules. The AM1 method is a semi-empirical method for quantum calculation of the electronic structures of molecules in computational chemistry and is a generalization of the modified neglect of differential diatomic overlap approximation (Dewar, M. J. S. et al., *Journal of the American Chemical Society*, 1985, 107, 3902).

The list of organic molecules calculated is shown in Table 11 below.

TABLE 11

Organic molecules used in training and verification for hydrogen abstraction (119 organic molecules)
List of organic molecules

| | |
|---|---|
| (3-amino-propyl)-dimethyl-amine | 1-chloro-4-methyl-pentane |
| (3-bromo-propyl)-dimethyl-amine | 1-chloro-butane |
| (3-chloro-propyl)-dimethyl-amine | 1-chloro-heptane |
| (3-fluoro-propyl)-dimethyl-amine | 1-chloro-hexane |
| (3-iodo-propyl)-dimethyl-amine | 1-chloromethyl-3-methyl-benzene |
| 1,2,3-trimethylbenzene | 1-chloromethyl-4-methyl-benzene |
| 1,2,4-trimethylbenzene | 1-chloro-octane |
| 1,2-difluoro-3-methyl-butane | 1-chloro-pentane |
| 1-bromo-2-methyl-benzene | 1-chloro-propane |
| 1-bromo-3-methyl-benzene | 1-ethoxy-3-fluoro-benzene |
| 1-bromo-4-methyl-benzene | 1-ethyl-4-methylbenzene |
| 1-bromo-4-methyl-pentane | 1-fluoro-2,4-dimethyl-pentane |
| 1-bromo-heptane | 1-fluoro-2-methyl-benzene |
| 1-bromo-hexane | 1-fluoro-2-methyl-octane |
| 1-bromo-octane | 1-fluoro-3-methyl-benzene |
| 1-bromo-pentane | 1-fluoro-4-methyl-butane |
| 1-bromo-propane | 1-fluoro-4-methyl-benzene |
| 1-chloro-2-methylbenzene | 1-fluoro-4-methyl-heptane |
| 1-chloro-3-methylbenzene | 1-fluoro-4-methyl-pentane |
| 1-chloro-4-methylbenzene | 1-fluoro-butane |
| 1,2,3-trimethylbenzene | Fluoro-benzene |
| 1,2,4-trimethylbenzene | Iodo-benzene |
| 1-ethyl-4-methylbenzene | mesitylene |
| 1-methyl-2-propylbenzene | methoxybenzene |
| 1-o-tolylpropan-1-one | m-xylene |
| 2,4-difluoro-1-methylbenzene | n,4-dimethylbenzenamine |
| 2-fluoro-phenylamine | o-xylene |
| 2-methylanisol | phenol |
| 3-fluoro-4-methylbenzeneamine | propylbenzene |
| 3-fluoro-phenylamine | p-toluidine |

TABLE 11-continued

Organic molecules used in training and verification for hydrogen abstraction (119 organic molecules)
List of organic molecules

| | |
|---|---|
| 4-ethoxy-aniline | p-xylene |
| 4-ethoxy-phenol | |
| 4-fluoro-phenylamine | |
| aniline | |
| benzene | |
| benzenethiol | |
| chloro-benzene | |
| cyanobenzene | |
| ethoxybenzene | |
| ethylbenzene | |

Such information was used to train and evaluate the empirical equations. These cases include methyl, primary, secondary and tertiary carbon atoms, etc., in various chemical environments.

The present inventors divided these cases into two types depending on whether electrically negative atoms (i.e. heteroatoms) exist around the breaking carbon-hydrogen bond.

Equations modeled with atomic descriptors through the correlation between effective atomic descriptors and quantum-mechanically calculated $E_a$ for hydrogen abstraction are shown in Tables 12 and 13 below.

TABLE 12

Correlation between effective atomic descriptors and quantum-mechanically calculated $E_a$ for hydrogen abstraction (the case of having no heteroatom in the alpha-position)

| | Training set | | |
|---|---|---|---|
| Atomic descriptor | $R^a$ | $RMSE^b$ | Equation |
| $\mu_{C-H}$ | 0.88 | 0.63 | $E_a^{Habs\_(A)} = 28.50 - 1.19*[\mu_{C-H}]$ |
| $\sum_i^{R.C.} \alpha_i$ | 0.67 | 1.00 | $E_a^{Habs\_(A)} = 28.50 - 0.90*\left[\sum_i^{R.C.} \alpha_i\right]$ |

$R^a$: correlation coefficient;
$RMSE^b$: root mean squared error.

TABLE 13

Correlation between effective atomic descriptors and quantum-mechanically calculated $E_a$ for hydrogen abstraction (the case of having a heteroatom in the alpha-position)

| | Training set | | |
|---|---|---|---|
| Atomic descriptor | $R^a$ | $RMSE^b$ | Equation |
| $\delta_{het}$ | 0.82 | 1.51 | $E_a^{Habs\_(B)} = 25.94 + 2.14*[\delta_{het}]$ |
| $\max(\delta_{heavy})$ | 0.57 | 2.16 | $E_a^{Habs\_(B)} = 25.94 + 1.51*[\max(\delta_{heavy})]$ |

$R^a$: correlation coefficient;
$RMSE^b$: root mean squared error.

The present inventors performed the training processes shown in Tables 12 and 13 above, thereby allowing linear equations to predict activation energy in various chemical environments using two normalized effective atomic descriptors suited to each case (equations 1-1 and 1-2 below).

Among these effective atomic descriptors, $[\delta_{het}]$, $[\max(\delta_{heavy})]$ and $[\mu_{C-H}]$ indicate the degree of weakness of the carbon-hydrogen bond, and $$\left[\sum_{i}^{R.C.} \alpha_i\right]$$

indicates the stability of transition states. In the present invention, all transition states were verified through the analysis of frequencies.

Figure 3:
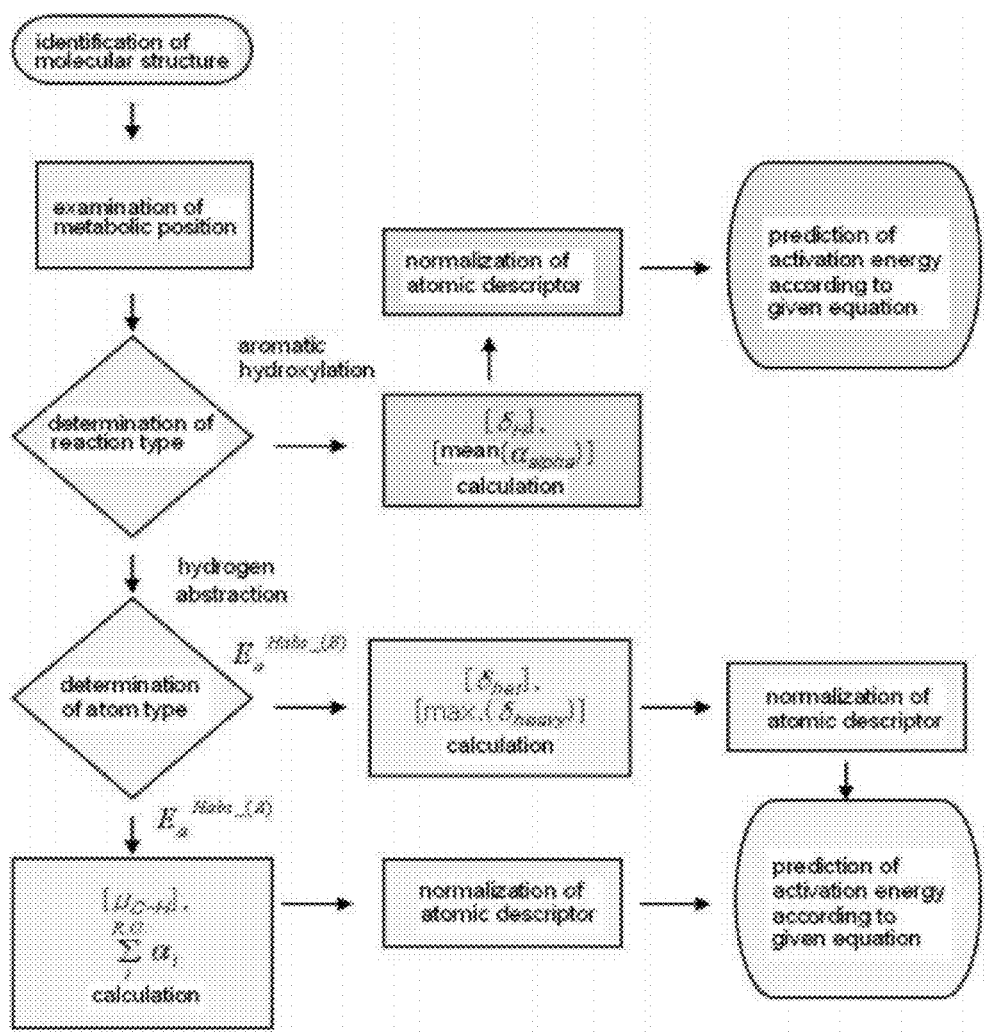
FIG. 3 is a flowchart showing a method of predicting activation energy using atomic descriptors according to the present invention.

FIG. 3 is a flowchart showing a method of predicting activation energy using the model of the present invention.

Specifically, the model for predicting the activation energy for CYP450-mediated hydrogen abstraction, developed in the present invention, comprises the following steps:
  i) examining the metabolic position of a target molecule;
  ii) determining the reaction type of the target molecule;
  iii) determining the atomic type depending on whether there is a heteroatom in the alpha-position relative to the reaction center of hydrogen abstraction;
  iv) if there is a heteroatom in the alpha-position, calculating the atomic descriptors $[\delta_{het}]$ and $[\max(\delta_{heavy})]$, and if there is no heteroatom in the alpha-position, calculating the atomic descriptors $[\mu_{C-H}]$ and $$\left[\sum_{i}^{R.C.} \alpha_i\right];$$

v) normalizing the atomic descriptors; and
  vi) predicting activation energy according to the following equations:

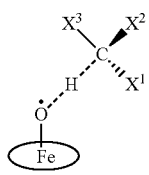

wherein the circle together with O—Fe indicates an oxyferryl intermediate;

$$E_a^{Habs\_(B)} = 25.94 + 1.88 * [\delta_{net}] + 1.03 * [\max(\delta_{heavy})] \quad \text{[Equation 1-1]}$$
$$R = 0.91, RMSE = 1.14, n = 62, P \text{ value} < 0.0001;$$

$$E_a^{Habs\_(A)} = 28.50 - 2.22 * [\mu_{C-H}] + 1.12 * \left[\sum_{i}^{R.C.} \alpha_i\right] \quad \text{[Equation 1-2]}$$
$$R = 0.95, RMSE = 0.43, n = 224, P \text{ value} < 0.0001$$

wherein $E_a^{Habs\_(B)}$ indicates the activation energy required for abstraction of hydrogen attached to a carbon atom having a heteroatom (an atom other than carbon) in the alpha-position relative to the reaction center; $E_a^{Habs\_(A)}$ indicates activation energy required for abstraction of hydrogen attached to a carbon atom having no heteroatom (an atom other than carbon) in the alpha-position relative to the reaction center; $[\delta_{het}]$ indicates the net atomic charge of a heteroatom (an atom other than carbon) in the alpha-position relative to the reaction center; $[\max(\delta_{heavy})]$ indicates the highest atomic charge in $X^1$, $X^2$ and $X^3$ which are neither hydrogen nor helium; $[\mu_{C-H}]$ indicates the bond dipole of the carbon-hydrogen bond; and $$\left[\sum_{i}^{R.C.} \alpha_i\right]$$

indicates the sum of the atomic polarizabilities of the atoms H, C, $X^1$, $X^2$ and $X^3$.

In equations 1-1 and 1-2 above, R: correlation coefficient; RMSE: root mean squared error; n: the number of atoms used in training; and P value: the significance of the correlation coefficient.

In step i), any C—H bond to the target molecule can be regarded as a position where metabolism can occur in the target molecule.

In step ii), if the carbon in any C—H bond to the target molecule is aliphatic carbon, it can be regarded as a position where H abstraction from the target molecule can occur.

In step iii), if there is a heteroatom in the alpha-position relative to the reaction center (C—H where actual metabolism occurs), equation 1-1 is used, and if there is no heteroatom in the alpha-position, equation 1-2 is used.

In step v), the term "normalization" refers to normalizing the mean of the values of atomic descriptors to zero (0) and the standard deviation to 1, from a statistical viewpoint. Namely, before prediction, normalization is carried out using the mean and, standard deviation of the values of the atomic descriptors used in the training of the prediction model of the present invention.

Figure 4:
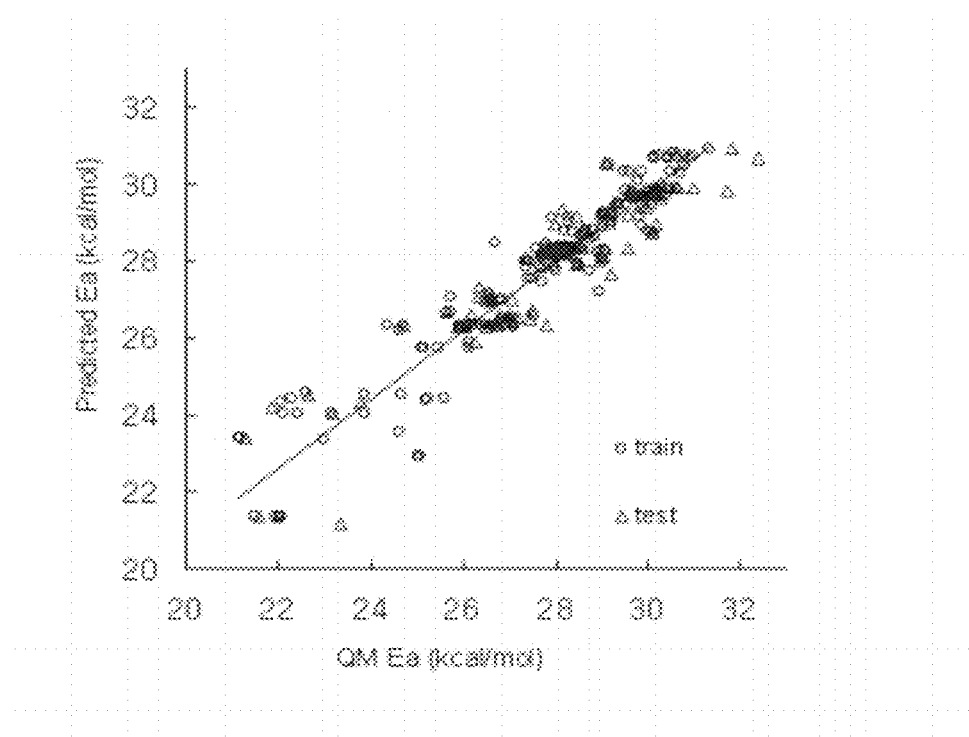
FIG. 4 shows the correlation between the quantum-mechanically calculated activation energy (QM $E_a$) for CYP450-mediated hydrogen abstraction and the activation energy (Predicted $E_a$) predicted according to the present invention.

As shown in FIG. 4, the activation energy predicted using the model of the present invention showed a high correlation with the quantum-mechanically calculated activation energy. 386 cases of 430 cases are within chemical accuracy (1 kcal per mol). Some inconsistent cases are attributable to interactions other than carbon-hydrogen-oxygen interactions during quantum mechanical calculation. Activation energies of various molecules in a gaseous state were calculated using Gaussian 03 [revision C.02, M. J. Frisch et al., Pittsburgh, Pa., USA, 2003].

Example 8

Verification of Activation Energy Predicted by Model for Predicting Activation Energy for Hydrogen Abstraction Activation energies for hydrogen abstraction from the following four molecules, predicted using the prediction model of Example 7, were verified by comparison with experimental values:

[Formula 3]

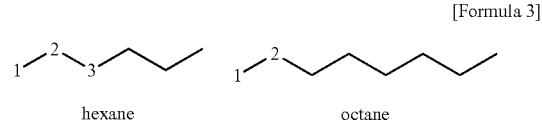

hexane        octane

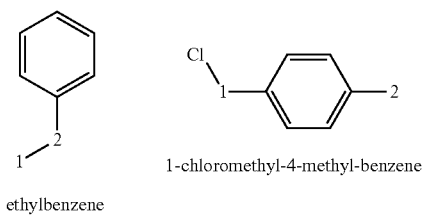

ethylbenzene 1-chloromethyl-4-methyl-benzene

TABLE 14

| Molecule | #[a] | Predicted activation energy[b] | Metabolic rate induced from activation energy[c] | Experimental metabolic rate[d] |
|---|---|---|---|---|
| Hexane | 1 | 26.89 | 4.1 | 4.5 |
|  | 2 | 28.20 | 46.6 | 49 |
|  | 3 | 28.16 | 49.3 | 46.5 |
| Octane | 1 | 29.69 | 8.2 | 2.5 |
|  | 2 | 28.21 | 91.8 | 97.5 |
| Ethylbenzene | 1 | 30.32 | 0.1 | 0.2 |
|  | 2 | 25.73 | 99.9 | 99.8 |
| 1-chloromathyl-4- | 1 | 27.51 | 12.5 | 16.0 |
| methyl-benzene | 2 | 26.31 | 87.5 | 84.0 |

[a]# indicates the atomic number of each molecule in formula 2;
[b]activation energy predicted by the method of the present invention;
[c]metabolic rate induced by introducing the predicted activation energy [b] into the Arrhenius equation; and
[d]in vitro experimental metabolic rate.

The experimental metabolic rates of the molecules shown in Table 14 above are already known in the art. Specifically, the experimental metabolic rate of hexane can be found in the literature [Ken-ichirou MOROHASHI, Hiroyuki SADANO, Yoshiie OKADA, Tsuneo OMURA. Position Specificity in n-Hexane Hydroxylation by two forms of Cytochrome P450 in Rat liver Microsomes. *J. Biochem.* 1983, 93, 413-419]; the experimental metabolic rate of octane in the literature [Jeffrey P. Jones, Allan E. Rettie, William F. Trager. Intrinsic Isotope Effects Suggest That the Reaction Coordinate Symmetry for the Cytochrome P-450 Catalyzed Hydroxylation of Octane Is Isozyme Independent. *J. Med. Chem.* 1990, 33, 1242-1246]; the experimental metabolic rate of ethylbenzene can be found in the literature [Ronald E. White, John P. Miller, Leonard V. Favreau, Apares Bhattacharyya. Stereochemical Dynamics of Aliphatic Hydroxylation by Cytochrome P-450. *J. AM. Chem. Soc.* 1986, 108, 6024-6031]; and the experimental metabolic rate of 1-chloromethyl-4-methyl-benzene can be found in the literature [LeeAnn Higgins, Kenneth R. Korzekwa, Streedhara Rao, Magong Shou, and Jeffrey P. Jones. An Assessment of the Reaction Energetics for Cytochrome P450-Mediated Reactions. *Arch. Biochem. Biophys.* 2001, 385, 220-230].

As can be seen in Table 14 above, when the metabolic rates[c] (induced by substituting into the Arrhenius equation the activation energies for hydrogen abstraction from the four molecules, hexane, octane, ethylbenzene and 1-chloromethyl-4-methyl-benzene, predicted according to the present invention) were compared with the experimental metabolic rates[d], these metabolic rates showed similar tendencies. This suggests that the experimental metabolic rates can be predicted through the activation energies predicted according to the present invention.

Example 9

Development of Model for Predicting the Activation Energy for Tetrahedral Intermediate Formation in Aromatic Hydroxylation The present inventors modeled tetrahedral intermediate formation serving as a good measure of the regioselectivity of aromatic hydroxylation in phase I metabolism.

[Reaction scheme 2]
Tetrahedral intermediate formation in cytochrome P450-mediated aromatic hydroxylation

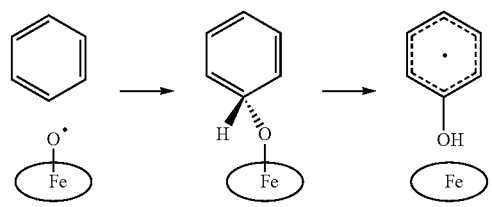

wherein the circle together with Fe—O indicates an oxyferryl intermediate.

To model the above reaction, the activation energies of 85 cases of 31 benzene molecules in various chemical environments were calculated using the AM1 (Austin Model 1) molecular orbital method.

Herein, the term "cases" refers to the number of atoms. For example, if there are 3 molecules having 3, 4 and 7 atoms, respectively, there will be 14 cases of 3 molecules. The AM1 method is a semi-empirical method for quantum calculation of the electronic structures of molecules in computational chemistry and is a generalization of the modified neglect of differential diatomic overlap approximation (Dewar, M. J. S. et al., *Journal of the American Chemical Society*, 1985, 107, 3902).

The list of organic molecules calculated is shown in Table 15 below.

TABLE 15

Organic molecules used in training and verification for tetrahedral intermediate formation (31 organic molecules)
List of organic molecules

| | |
|---|---|
| 1,2,3-trimethylbenzene | Fluoro-benzene |
| 1,2,4-trimethylbenzene | Iodo-benzene |
| 1-ethyl-4-methylbenzene | mesitylene |
| 1-methyl-2-propylbenzene | methoxybenzene |
| 1-o-tolylpropan-1-one | m-xylene |
| 2,4-difluoro-1-methylbenzene | n,4-dimethylbenzenamine |
| 2-fluoro-phenylamine | o-xylene |
| 2-methylanisol | phenol |
| 3-fluoro-4-methylbenzenamine | propylbenzene |
| 3-fluoro-phenylamine | p-toluidine |
| 4-ethoxyaniline | p-xylene |
| 4-ethoxy-phenol | |
| 4-fluoro-phenylamine | |
| aniline | |
| benzene | |
| benzenethiol | |
| chloro-benzene | |
| cyanobenzene | |
| ethoxybenzene | |
| ethylbenzene | |

Such information was used to train and evaluate the empirical equations. These cases were divided into three types: i)

having one substituent in the ortho/para position; ii) having one substituent in the meta-position; and iii) having 0, 2 or 3 substituents.

Equations modeled with atomic descriptors through the correlation between effective atomic descriptors and quantum-mechanically calculated $E_a$ for aromatic hydroxylation are shown in Tables 16, 17 and 18 below.

TABLE 16

Correlation between effective atomic descriptors and quantum-mechanically calculated $E_a$ for aromatic hydroxylation (the case of having a substituent in the ortho-position)

| | Training set | | |
|---|---|---|---|
| Atomic descriptor | $R^a$ | $RMSE^b$ | Equation |
| $\delta_H$ | 0.08 | 1.31 | $E_a^{aro\_o,p} = 14.67 + 63.33 * [\delta_H]$ |
| $\alpha_{alpha}$ | 0.57 | 1.07 | $E_a^{aro\_o,p} = 61.60 - 26.53 * [\alpha_{alpha}]$ |

$R^a$: correlation coefficient;
$RMSE^b$: root mean squared error.

TABLE 17

Correlation between effective atomic descriptors and quantum-mechanically calculated $E_a$ for aromatic hydroxylation (the case of having a substituent in the meta-position)

| | Training set | | |
|---|---|---|---|
| Atomic descriptor | $R^a$ | $RMSE^b$ | Equation |
| $\delta_H$ | 0.03 | 0.56 | $E_a^{aro\_m} = -12.61 + 333.87 * [\delta_H]$ |
| $\alpha_{alpha}$ | 0.50 | 0.49 | $E_a^{aro\_m} = 132.75 - 72.54 * [\alpha_{alpha}]$ |

$R^a$: correlation coefficient;
$RMSE^b$: root mean squared error.

TABLE 18

Correlation between effective atomic descriptors and quantum-mechanically calculated $E_a$ for aromatic hydroxylation (the case of having 0, 2 or 3 substituents)

| | Training set | | |
|---|---|---|---|
| Atomic descriptor | $R^a$ | $RMSE^b$ | Equation |
| $\delta_H$ | 0.69 | 0.95 | $E_a^{aro\_0,2,3} = 70.00 - 465.88 * [\delta_H]$ |
| $\alpha_{alpha}$ | 0.05 | 1.31 | $E_a^{aro\_0,2,3} = 17.65 + 2.21 * [\alpha_{alpha}]$ |

$R^a$: correlation coefficient;
$RMSE^b$: root mean squared error.

The present inventors performed the training processes shown in Tables 16 to 18 above, thereby allowing linear equations to predict activation energy in various chemical environments using two normalized effective atomic descriptors suited to each case (equations 2-1, 2-2 and 2-3 below).

Among effective atomic descriptors which are used in the equations for predicting the activation energy for tetrahedral intermediate formation, $[\delta_H]$ determines the proximity between oxygenating species and substrate, and [mean($\alpha_{alpha}$)] is related to the stability of transition states. In the present invention, para-nitrosophenoxy radical (PNR) was used as oxygenating species, and all transition states were verified through the analysis of frequencies.

FIG. 3 shows a flowchart showing a method of predicting activation energy using the model used in the present invention.

Specifically, the model for predicting the activation energy for tetrahedral intermediate formation in CYP450-mediated aromatic hydroxylation, developed in the present invention, comprises the following steps:

i) examining the metabolic position of a target molecule;
ii) determining the reaction type of the target molecule;
iii) if the reaction type in step ii) is determined to be aromatic hydroxylation, calculating the atomic descriptors $[\delta_H]$ and [mean($\alpha_{alpha}$)];
iv) normalizing the atomic descriptors; and
v) predicting activation energy according to the following equations:

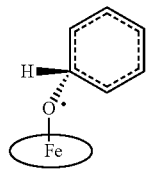

wherein the circle together with Fe—O indicates an oxyferryl intermediate;

$E_a^{aro\_o,p} = 21.34 - 0.75*[\delta_H] - 1.24*[\text{mean}(\alpha_{alpha})]$

R=0.71, RMSE=0.95, n=16, P value=0.009; [Equation 2-1]

$E_a^{aro\_m} = 22.14 - 0.68*[\delta_H] - 0.83*[\text{mean}(\alpha_{alpha})]$

R=0.88, RMSE=0.30, n=8, P value=0.026; [Equation 2-2]

$E_a^{aro\_0,2,3} = 21.02 - 1.49*[\delta_H] - 0.92*[\text{mean}(\alpha_{alpha})]$ R=0.87, RMSE=0.65, n=33, P<0.0001 [Equation 2-3]

wherein $E_a^{aro\_o,p}$ indicates the activation energy for tetrahedral intermediate formation in a benzene having one substituent in the ortho/para position; $E_a^{aro\_m}$ indicates the activation energy for tetrahedral intermediate formation in a benzene having one substituent in the meta-position; $E_a^{aro\_0,2,3}$ indicates the activation energy for tetrahedral intermediate formation in a benzene having 0, 2 or 3 substituents; $[\delta_H]$ indicates the net atomic charge of the hydrogen; and [mean($\alpha_{alpha}$)] indicates the mean of the polarizabilities of adjacent carbon atoms.

In equations 2-1, 2-2 and 2-3 above, R: correlation coefficient; RMSE: root mean squared error; n: the number of atoms used in training; and P value: the significance of the correlation coefficient.

Figure 5:
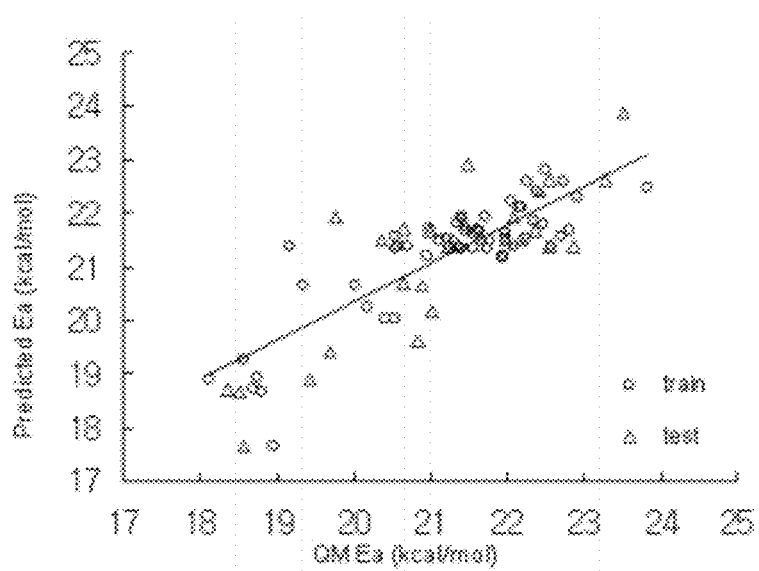
FIG. 5 shows the correlation between the quantum-mechanically calculated activation energy (QM $E_a$) for CYP450-mediated aromatic hydroxylation and the activation energy (Predicted $E_a$) predicted according to the present invention.

As shown in FIG. 5, the activation energy predicted using the model of the present invention showed a high correlation with the quantum-mechanically calculated activation energy. 70 cases of 85 cases are within chemical accuracy (1 kcal per mol). Some inconsistent cases occurred because the model did not consider the ortho-, meta- and para-effects when modeling the benzene molecule having 0, 2 or 3 substituents. Activation energies of various molecules in a gaseous state were calculated using Gaussian 03 [revision C.02, M. J. Frisch et al., Pittsburgh, Pa., USA, 2003].

Example 10

Verification of Activation Energy Predicted by Model for Predicting Activation Energy for Tetrahedral Intermediate Formation in Aromatic Hydroxylation The activation energies for tetrahedral intermediate formation for the following two molecules, predicted by the prediction model of Example 9, were verified by comparison with experimental values.

[Formula 4]

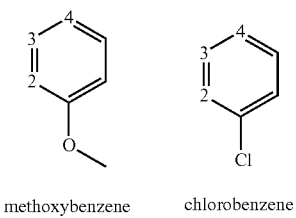

methoxybenzene     chlorobenzene

TABLE 19

| Molecule | #[a] | Predicted activation energy[b] | Metabolic rate induced from activation energy[c] | Experimental metabolic rate[d] |
|---|---|---|---|---|
| Methoxybenzene | 2 | 21.79 | 30.8 | 15-24 |
|  | 3 | 22.41 | 11.1 | 1-3 |
|  | 4 | 21.40 | 58.1 | 62-75 |
| Chlorobenzene | 2 | 22.81 | 8.0 | 17-19 |
|  | 3 | 22.58 | 11.6 | 5-9 |
|  | 4 | 21.39 | 80.4 | 71-79 |

[a]# indicates the atomic number of each molecule in formula 4;
[b]activation energy predicted by the method of the present invention;
[c]metabolic rate induced by introducing the predicted activation energy [b] into the Arrhenius equation; and
[d]in vitro experimental metabolic rate.

The experimental metabolic rates of the molecules shown in Table 19 above are already known in the art. Specifically, the experimental metabolic rate of methoxybenzene can be found in the literature [Robert P. Hanzlik, Kerstin Hogberg, Charles M. Judson. Microsomal hydroxylation of specifically deuterated monosubstituted benzenes. Evidence for direct aromatic hydroxylation. *Biochemistry.* 1984, 23, 3048-3055]; and the chlorobenzene can be found in the literature [H. G. Selander, D. M. Jerina, J. W. Daly. Metabolism of Chlorobenzene with Hepatic Microsomes and Solubilized Cytochrome P-450 Systems. *Arch. Biochem. Biophys.* 1975, 168, 309-321].

As can be seen in Table 19 above, when the metabolic rates (induced by substituting into the Arrhenius equation the activation energies for hydrogen abstraction from the two molecules, methoxybenzene and chorobenzene, predicted according to the present invention) were compared with the experimental metabolic rates[d], these metabolic rates showed similar tendencies. This suggests that the experimental metabolic rates can be predicted through the activation energies predicted according to the present invention.

As described above, the method of the present invention can rapidly predict activation energy for phase I metabolites at a practical level without having to perform a docking experiment between any additional CYP450 and the substrate, or a quantum mechanical calculation, thereby making it easier to develop new drugs using a computer. Also, the present invention may propose a strategy for increasing the bioavailability of drugs through the avoidance of metabolites based on the possibility of drug metabolism. Furthermore, the method of the present invention proposes new empirical approaches which can also be easily applied to activation energies for various chemical reactions, and makes it possible to explain physical and chemical factors that determine activation energy. In addition, through the prediction of activation energy according to the present invention, it is possible to predict i) metabolic products, ii) the relative rate of metabolism, iii) metabolic regioselectivity, iv) metabolic inhibition, v) drug-drug interactions, and vi) the toxicity of a metabolite.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within the scope of the present invention.

What is claimed is:

1. A method for constructing a database of atomic fingerprint descriptors by a processor for predicting a reaction rate for a cytochrome P450-mediated reaction on a substrate, the method comprising the steps of:

(i) providing an atomic fingerprint descriptor of a substrate, which is obtained by characterizing one or more atomic positions of the substrate according to the following Equation 1:

$$Xabc \quad \text{[Equation 1]}$$

wherein X is the chemical symbol of an atom; a is a bond indicator noting the number of atoms bonded; b is a ring indicator noting whether the atom is part of a ring; and c is an aromatic indicator noting whether the atom is an aromatic atom;

(ii) calculating an activation energy for the one or more atomic positions of step (i) based on two or more atomic descriptors which valuate atomic interactions at said atomic position, wherein the two or more atomic descriptors are selected from the group consisting of $[\delta_{het}]$, $[\max(\delta_{heavy})]$, $[\mu_{C-H}]$, $$\left[\sum_{i}^{R.C.} \alpha_i\right],$$

$[\delta_H]$, and [mean ($\alpha_{alpha}$)];

(iii) predicting a reaction rate for a cytochrome P450-mediated reaction by introducing the calculated activation energy obtained in step (ii) into an Arrhenius equation;

(iv) performing a statistical correlation which relates the predicted reaction rate of step (iii) with an experimental reaction rate; and (v) storing the predicted reaction rate, the experimental reaction rate, and the statistical correlation for each atomic fingerprint descriptor of the substrate, into a database of atomic fingerprint descriptors for predicting reaction rates for cytochrome P450-mediated reactions of a substrate.

2. The method of claim 1, wherein the cytochrome P450-mediated reaction on a substrate is aliphatic hydroxylation or aromatic hydroxylation.

3. The method of claim 1, wherein the cytochrome P450-mediated reaction on a substrate is N-dealkylation, C-hydroxylation, N-oxidation, or O-dealkylation.

4. The method of claim 1, wherein an enzyme catalyzing the cytochrome P450-mediated reaction is selected from the group consisting of CYP2E1, CYP3A4, CYP2B6, CYP2C8, CYP2C9, CYP1A1, CYP1A2, CYP2C19, CYP2D6, CYP1B1, and CYP2A6.

5. The method of claim 1, wherein the cytochrome P450-mediated reaction is a cytochrome P450-mediated hydrogen abstraction on a substrate of the following Formula 1:

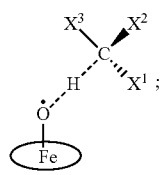

[Formula 1]

wherein the circle together with Fe—O indicates an oxyferryl intermediate;
wherein the two or more atomic descriptors are $[\delta_{het}]$, $[\max(\delta_{heavy})]$, $[\mu_{C-H}]$, and $$\left[\sum_{i}^{R.C.} \alpha_i\right];$$

and
wherein $[\delta_{het}]$ indicates the net atomic charge of a heteroatom in the alpha-position relative to the reaction center, $[\max(\delta_{heavy})]$, indicates the highest atomic charge in $X^1$, $X^2$ and $X^3$ which are neither hydrogen nor helium, $[\mu_{C-H}]$ indicates the bond dipole of the carbon-hydrogen bond, and $$\left[\sum_{i}^{R.C.} \alpha_i\right]$$

indicates the sum of the atomic polarizabilities of H, C, $X^1$, $X^2$ and $X^3$.

6. The method of claim 5, wherein the activation energy is calculated in step (ii) according to the following equation:

$$E_a^{Habs\_(B)} = 25.94 + 1.88*[\delta_{het}] + 1.03*[\max(\delta_{heavy})]$$

wherein $E_a^{Habs\_(B)}$ indicates activation energy required for abstraction of hydrogen attached to a carbon atom having a heteroatom in the alpha-position relative to the reaction center.

7. The method of claim 5, wherein the activation energy is calculated in step (ii) according to the following equation:

$$E_a^{Habs\_(A)} = 28.50 - 2.22*[\mu_{C-H}] + 1.12*\left[\sum_{i}^{R.C.} \alpha_i\right]$$

wherein $E_a^{Habs\_(A)}$ indicates activation energy required for abstraction of hydrogen attached to a carbon atom having no heteroatom in the alpha-position relative to the reaction center.

8. The method of claim 1, wherein the cytochrome P450-mediated reaction is formation of a tetrahedral intermediate which occurs via a cytochrome P450-mediated aromatic hydroxylation on a substrate of the following Formula 2:

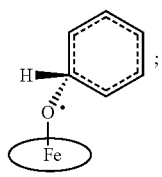

[Formula 2]

wherein the circle together with Fe—O indicates an oxyferryl intermediate;
wherein the two or more atomic descriptors are $[\delta_H]$ and $[\text{mean}(\alpha_{alpha})]$; and
wherein $[\delta_H]$ indicates the net atomic charge of the hydrogen of the substrate and $[\text{mean}(\alpha_{alpha})]$ indicates the mean value of the polarizabilities of adjacent carbon atoms.

9. The method of claim 8, wherein the activation energy is calculated in step (ii) according to the following equation:

$$E_a^{aro-o,p} = 21.34 - 0.75*[\delta_H] - 1.24*[\text{mean}(\alpha_{alpha})]$$

wherein $E_a^{aro-o,p}$ indicates the activation energy for tetrahedral intermediate formation in a benzene having one substituent in the ortho/para-position.

10. The method of claim 8, wherein the activation energy is calculated in step (ii) according to the following equation:

$$E_a^{aro-m} = 22.14 - 0.68*[\delta_H] - 0.83*[\text{mean}(\alpha_{alpha})]$$

wherein $E_a^{aro-m}$ indicates the activation energy for tetrahedral intermediate formation in a benzene having one substituent in the meta-position.

11. The method of claim 8, wherein the activation energy is calculated in step (ii) according to the following equation:

$$E_a^{aro-0,2,3} = 21.02 - 1.49*[\delta_H] - 0.92*[\text{mean}(\alpha_{alpha})]$$

wherein $E_a^{aro-0,2,3}$ indicates the activation energy for tetrahedral intermediate formation in a benzene having 0, 2, or 3 substituents.

12. A method for a processor to calculate an activation energy for a cytochrome P450-mediated hydrogen abstraction on a substrate of the following Formula 1:

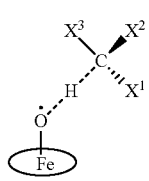

[Formula 1]

wherein the circle together with Fe—O indicates an oxyferryl intermediate; and wherein the atomic position comprises two or more atomic descriptors selected from the group consisting of [δ$_{het}$], [max(δ$_{heavy}$)], [μ$_{C—H}$], and $$\left[\sum_{i}^{R.C.} \alpha_i\right];$$

and
wherein [δ$_{het}$] indicates the net atomic charge of a heteroatom in the alpha-position relative to the reaction center, [max(δ$_{heavy}$)] indicates the highest atomic charge in X$^1$, X$^2$ and X$^3$ which are neither hydrogen nor helium, [μ$_{C—H}$] indicates the bond dipole of the carbon-hydrogen bond, and $$\left[\sum_{i}^{R.C.} \alpha_i\right]$$

indicates the sum of the atomic polarizabilities of the atoms H, C, X$^1$, X$^2$ and X$^3$;
the method further comprise making a comparison of the calculated activation energy to a database of atomic fingerprint descriptors;
wherein the comparison provides a prediction regarding one or more of metabolic products, relative rate of metabolism, metabolic regioselectivity, metabolic inhibition, drug-drug interactions, and toxicity of a metabolite.

13. The method of claim 12, wherein the cytochrome P450-mediated hydrogen abstraction is catalyzed by a cytochrome P450 enzyme selected from the group consisting of CYP2E1, CYP3A4, CYP2B6, CYP2C8, CYP2C9, CYP1A1, CYP1A2, CYP2C19, CYP2D6, CYP1B1, and CYP2A6.

14. The method of claim 12, wherein hydrogen abstraction can occur if a C atom of a C—H bond in the substrate is an aliphatic carbon.

15. The method of claim 12, wherein the two or more atomic descriptors are [δ$_{het}$] and [max(δ$_{heavy}$)] when there is a heteroatom in the alpha-position relative to the reaction center and wherein the activation energy is calculated according to the following equation:

$E_a^{Habs\_(B)}$=25.94+1.88*[δ$_{het}$]+1.03*[max(δ$_{heavy}$)].

16. The method of claim 12, wherein the two or more atomic descriptors are [μ$_{C—H}$] and $$\left[\sum_{i}^{R.C.} \alpha_i\right]$$

when there is no heteroatom in the alpha-position relative to the reaction center and wherein the activation energy is calculated according to the following equation:

$$E_a^{Habs\_(A)} = 28.50 - 2.22 * [\mu_{C-H}] + 1.12 * \left[\sum_{i}^{R.C.} \alpha_i\right].$$

17. A method for a processor to calculate an activation energy for formation of a tetrahedral intermediate by a cytochrome P450-mediated aromatic hydroxylation at an atomic position in a substrate of the following Formula 2:

[Formula 2]

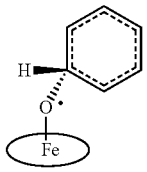

wherein the circle together with Fe—O indicates an oxyferryl intermediate;
wherein the atomic position comprises atomic descriptors [δ$_H$] and [mean(α$_{alpha}$)]; and
wherein [δ$_H$] indicates the net atomic charge of the hydrogen of the substrate and [mean(α$_{alpha}$)] indicates the mean values of polarizabilities of adjacent carbon atoms;
the method further comprises making a comparison of the calculated activation energy to a database of atomic fingerprint descriptors;
wherein the comparison provides a prediction regarding one or more of metabolic products, relative rate of metabolism, metabolic regioselectivity, metabolic inhibition, drug-drug interactions, and toxicity of a metabolite.

18. The method of claim 17, wherein the cytochrome P450-mediated aromatic hydroxylation is catalyzed by a cytochrome P450 enzyme selected from the group consisting of CYP2E1, CYP3A4, CYP2B6, CYP2C8, CYP2C9, CYP1A1, CYP1A2, CYP2C19, CYP2D6, CYP1B1, and CYP2A6.

19. The method of claim 17, wherein aromatic hydroxylation can occur if a C atom of a C—H bond in the substrate is an aliphatic carbon.

20. The method of claim 17, wherein the atomic descriptors [δ$_H$] and [mean(α$_{alpha}$)] are determined.

21. The method of claim 20, wherein the activation energy is calculated according to the following equation:

$E_a^{aro—o,p}$=21.34−0.75*[δ$_H$]−1.24*[mean(α$_{alpha}$)]

wherein $E_a^{aro—o,p}$ indicates the activation energy for tetrahedral intermediate formation in a benzene having one substituent in the ortho/para-position.

22. The method of claim 20, wherein the activation energy is calculated according to the following equation:

$E_a^{aro—m}$=22.14−0.68*[δ$_H$]−0.83*[mean(α$_{alpha}$)]

wherein $E_a^{aro—m}$ indicates the activation energy for tetrahedral intermediate formation in a benzene having one substituent in the meta-position.

23. The method of claim 20, wherein the activation energy is calculated according to the following equation:

$E_a^{aro—0,2,3}$=21.02−1.49*[δ$_H$]−0.92*[mean(α$_{alpha}$)]

wherein $E_a^{aro—0,2,3}$ indicates the activation energy for tetrahedral intermediate formation in a benzene having 0, 2, or 3 substituents.

* * * * *